(12) United States Patent
Zion et al.

(10) Patent No.: US 7,531,191 B2
(45) Date of Patent: May 12, 2009

(54) STIMULI-RESPONSIVE SYSTEMS FOR CONTROLLED DRUG DELIVERY

(75) Inventors: Todd C. Zion, Allston, MA (US); Andrey Zarur, Winchester, MA (US); Jackie Y. Ying, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 575 days.

(21) Appl. No.: 10/740,436

(22) Filed: Dec. 17, 2003

(65) Prior Publication Data

US 2004/0202719 A1 Oct. 14, 2004

Related U.S. Application Data

(60) Provisional application No. 60/434,076, filed on Dec. 17, 2002.

(51) Int. Cl.
*A61K 9/10* (2006.01)
*A61K 9/14* (2006.01)

(52) U.S. Cl. .................... 424/488; 424/486; 424/489

(58) Field of Classification Search ............... 424/490, 424/493, 177–178, 484–489; 260/112.7; 514/944
See application file for complete search history.

(56) References Cited

U.S. PATENT DOCUMENTS

| | | | | | |
|---|---|---|---|---|---|
| 4,348,387 | A | * | 9/1982 | Brownlee et al. | 514/4 |
| 5,641,515 | A | * | 6/1997 | Ramtoola | 424/489 |
| 5,707,644 | A | * | 1/1998 | Illum | 424/434 |
| 5,814,449 | A | | 9/1998 | Schultz et al. | |
| 5,830,506 | A | * | 11/1998 | Taylor | 424/488 |
| 5,902,607 | A | | 5/1999 | Taylor | |
| 6,063,116 | A | | 5/2000 | Kelleher | 623/4 |
| 6,221,397 | B1 | * | 4/2001 | Russell-Jones et al. | 424/486 |
| 6,410,053 | B1 | * | 6/2002 | Taylor | 424/488 |
| 6,454,710 | B1 | | 9/2002 | Ballerstadt et al. | |
| 6,671,527 | B2 | | 12/2003 | Petersson et al. | |
| 2002/0168409 | A1 | | 11/2002 | Taylor | |

FOREIGN PATENT DOCUMENTS

| | | |
|---|---|---|
| EP | 0626862 B1 | 1/1999 |
| EP | 0706401 B1 | 11/2002 |
| WO | WO-93/13803 | 7/1993 |
| WO | WO-95/01186 | 1/1995 |

OTHER PUBLICATIONS

Kenneth J. Armstrong, Matthew W.Noall, and John E. Stouffer, Dextran-linked insulin: A soluble high molecular weight derivative with biological activity in vivo and in vitro, vol. 47, 354-360, 1972, Biochemical and Biophysical Res. Commun.*
John Plckup, Lydia Mccartney, Olaf Rolinski, and David Birch, In vivo glucose sensing for diabetes management: progress towares non-invasive monitoring, BMJ 1999; 319:1289.*
Kenneth J. Armstrong, Matthew W. Noall and John E Stouffer, Dextran-linked isulin: A soluble high molecular weight derivative with biological activity in vivo and in vitro, Biochemical and Biophysical Research Coomunications, 47, 354-360, 1972).*
Jung Ju Kim and Kinam Park, Modulated insulin delivery from glucose-sensitive hydrogel dosage forms, Journal of Controlled Release, 77, 39-47, 2001.*
Fujio Suzuki, Yasushi Daikuhara, Masyoshi Ono, and Yoshiro Takeda, Studies on the Mode of Action of Insulin: Properties and Biological Activity of an Insulin-Dextran Complex, Endocrinology, 1972, 90(5), 1220-1230.*
Kenneth J. Armstron, Mathew W. Noall and John E. Stouffer, Dextran-linked Isulin: A Soluble high molecular weight derivative with bilogical activity in vivo and in vitro, Biochemical and Biophysical Research Communications, 47, 354-360, 1972.*
Jung Ju Kim and Kinam Park, Modulated insulin delivery from glucose-sensitive hydrogel dosage forms, Jorunal of COntrolled Release, 77, 39-47, 2001.*
Allen, et al., "Binding of Rat and Human Surfactant Proteins A and D to *Aspergillus fumigatus Conidia*", *Infection and Immunity*, 67(9): 4563-4569, 1999.
Armstrong, et al., "Dextran-linked insulin: a soluble high molecular weight derivative with biological activity in vivo and in vitro", *Biochem. Biophys. Res. Commun.* 47: 354, 1972.
Baudys, et al., "Extending Insulin Action in Vivo by Conjugation to Carboxymethyl Dextran", *Bioconjugate Chem.* 9: 176-183, 1998.
De Jong, et al., "Physically Crosslinked Dextran Hydrogels by Stereocomplex Formation of Lactic Acid Oligomers: Degradation and Protein Release Behavior", *Journal of Controlled Release*, 71: 261-275, 2001.
Dillman, et al., "Preclinical Trials with Combinations and Conjugates of T101 Monoclonal Antibody and Doxorubicin", *Cancer Research*, 46: 4886-4891, 1986.
Dumestre-Perard, et al., "Evaluation and Clinical Interest of Mannan Binding Lectin Function in Human Plasma", *Molecular Immunology*, 39: 465-473, 2002.
Eda, et al., "Characterization of Truncated Human Mannan-Binding Protein (MBP) Expressed in *Escherichia coli*", *Biosci. Biotechnol. Biochem.* 62(7): 1326-1331, 1998.
Eda, et al., "Recombinant bovine conglutinin, lacking the N-terminal and collagenous domains, has less conglutination activity but is able to inhibit haemagglutination by influenza A virus", *Biochem J.* 316:43-48, 1996.

(Continued)

*Primary Examiner*—Michael G Hartley
*Assistant Examiner*—Jagadishwar R Samala
(74) *Attorney, Agent, or Firm*—Choate, Hall & Stewart LLP; Charles E. Lyon, DPhil, JD

(57) ABSTRACT

A method of delivering a therapeutic agent by providing a cross-linked polymer encapsulating the therapeutic agent to a site in a patient. The degradation rate of the cross-linked polymer is correlated with a local concentration of an indicator, and the therapeutic agent is released as the cross-linked polymer degrades.

49 Claims, 24 Drawing Sheets

OTHER PUBLICATIONS

Eda, et al., "Structure of a truncated human surfactant protein D is less effective in agglutinating bacteria than the native structure and fails to inhibit haemagglutination by influenza A virus", *Biochem J.* 323:393-399, 1997.

Engel, et al., "The Crystal Structure of Dipeptidyl Peptidase IV (CD26) Reveals is Functional Regulation and Enzymatic Mechanism", *PNAS*, 100(9): 5063-5068, 2003.

Halestrap, et al., "The Proton Linked Monocarboxylate Transporter (MCT) Family: Structure, Function and Regulation", *Biochem. J.*, 343: 281-299, 1999.

Harada, et al., "Determinants for the Drug Release from T-0128, Camptothecin Analogue-Carboxymethyl Dextran Conjugate", *Journal of Controlled Release*, 69: 399-412, 2000.

Huynh, et al., "Carboxymethylation of Dextran in Aqueous Alcohol as the First Step of the Preparation of Derivatized Dextrans", *Die Angewandte Makromolekulare Chemie*, 254: 61-65, 1998.

Kagedal, et al., "Binding of Covalent Proteins to Polysaccharides by Cyanogen Bromide and Organic Cyanates. I. Preparation of Soluble Glycine-, Insulin- and Ampicillin-Dextran", *Acta Chemica Scandinavica*, 25: 1855-1859, 1971.

Kim and Park, "Glucose-binding property of pegylated concanavalin A", *Pharmaceutical Research* 18: 794, 2001.

Kim and Park, "Modulated insulin delivery from glucose-sensitive hydrogel dosage forms", *J. Controlled Release* 77: 39, 2001.

Looger, et al., "Computational Design of Receptor and Sensor Proteins with Novel Functions", *Nature*, 423: 185-190, 2003.

Medina-Bolivar, et al., "A non-toxic lectin for antigen delivery of plant-based mucosal vaccines", *Vaccine* 21: 997-1005, 2003.

Mehvar, et al., "Molecular-Weight-Dependent Pharmacokinetics of Fluorescein-Labeled Dextrans in Rats", *Journal of Pharmaceutical Sciences*, 81(9): 908-912, 1992.

Mislovicova, et al., "Neoglycoconjugates of Mannan with Bovine Serum Albumin and Their Interaction with Lectin Concanavalin A", *Bioconjugate Chem.* 13: 136-142, 2002.

Mitra, et al., "Tumour Targeted Delivery of Encapsulated Dextran-Doxorubicin Conjugate Using Chitosan Nanoparticles as Carrier", *Journal of Controlled Release*, 74: 317-323, 2001.

Ohya, et al., "Design of Macromolecular Prodrug of Cisplatin Using Dextran with Branched Galactose Units as Targeting Moieties to Hepatoma Cells", *Biomacromolecules*, 2: 927-933, 2001.

Persson, et al., "Surfactant Protein D is a Divalent Cation-Dependent Carbohydrate-Binding Protein", *The Journal of Biological Chemistry*, 265(10): 5755-5760, 1990.

Sakamoto, et al., "Comparative Effects of Native Insulin and Insulin-Dextran Complexes on the Metabolism of Adipose Tissue", *Biochimica et Biophysica Acta*, 498: 102-113, 1977.

Salins, et al., "A Novel Reagentless Sensing System for Measuring Glucose Based on the Galactose/Glucose-Binding Protein", *Analytical Biochemistry*, 294: 19-26, 2001.

Sheriff, et al., "Human Mannose-Binding Protein Carbohydrate Recognition Domain Trimerizes Through a Triple α-Helical Coiled-Coil", *Structural Biology*, 1(11): 789-794, 1994.

Sugahara, et al., "Characteristics of Tissue Distribution of Various Polysaccharides as Drug Carriers: Influences of Molecular Weight and Anionic Charge on Tumor Targeting", *Biol. Pharm. Bull.* 24(5): 535-543, 2001.

Suzuki, et al., "Studies on the mode of insulin: properties and biological activity of an insulin-dextran complex", *Endocrinology* 90: 1220-1230, 1972.

Tanna, et al., "Covalent coupling of concanavalin A to a Carbopol 934P and 941P carrier in glucose-sensitive gels for delivery of insulin", *J. Pharm. Pharmacol.* 11: 1461, 2002.

Thoma, et al., "Versatile Functionalization of Polylysine: Synthesis, Characterization, and Use of Neoglycoconjugates", *J. Am. Chem. Soc.* 121: 5919-5929, 1999.

Ueno, et al., "Polyethylene glycol-modified pokeweed mitogen (PWM) as a potential non-immunogenic stimulator of lymphokine-activated killer cells", *J. Biomater. Sci. Polymer Edn.* 7: 753, 1996.

Zion, et al., "Bio-Inspired Nanoscale Hybrid Systems", *Materials Research Society*, Fall Meeting, Boston, MA, Dec. 2-4, 2002.

* cited by examiner

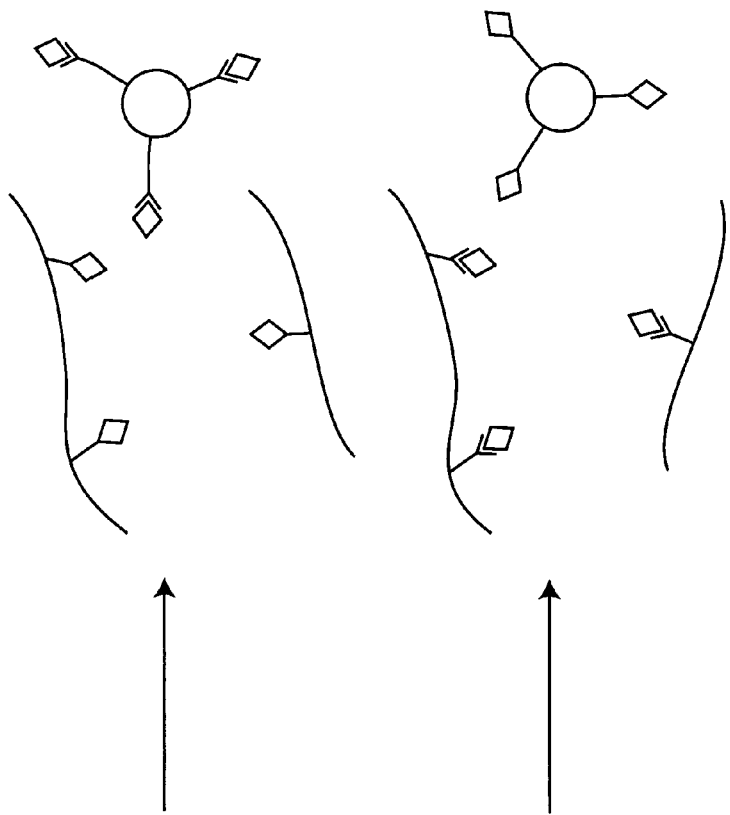
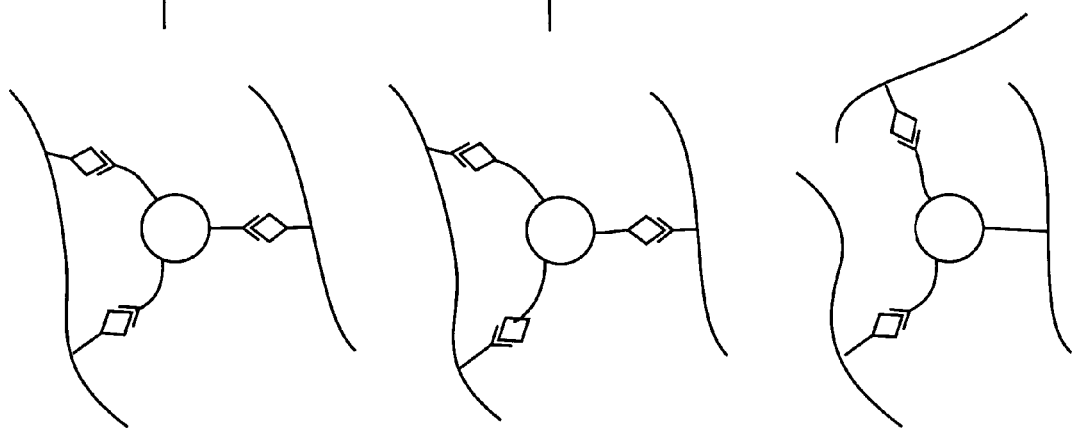
FIG. 1A  FIG. 1B  FIG. 1C

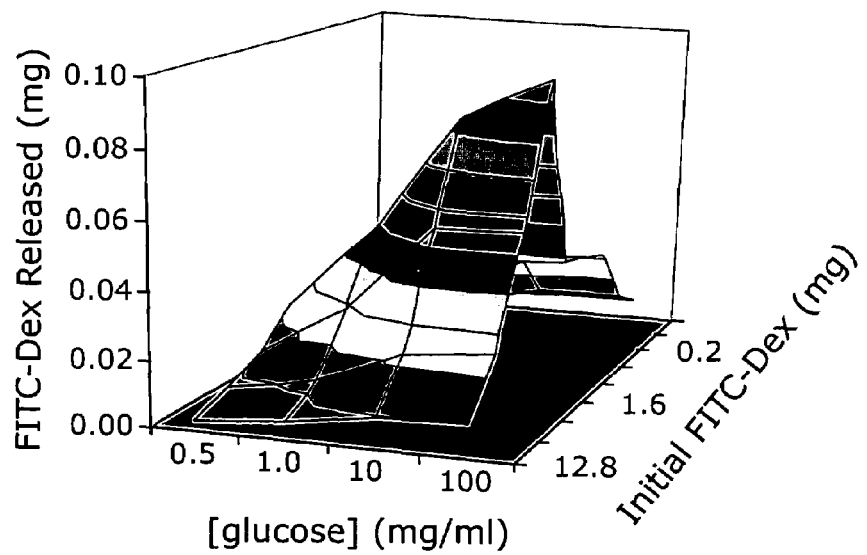
FIG. 26
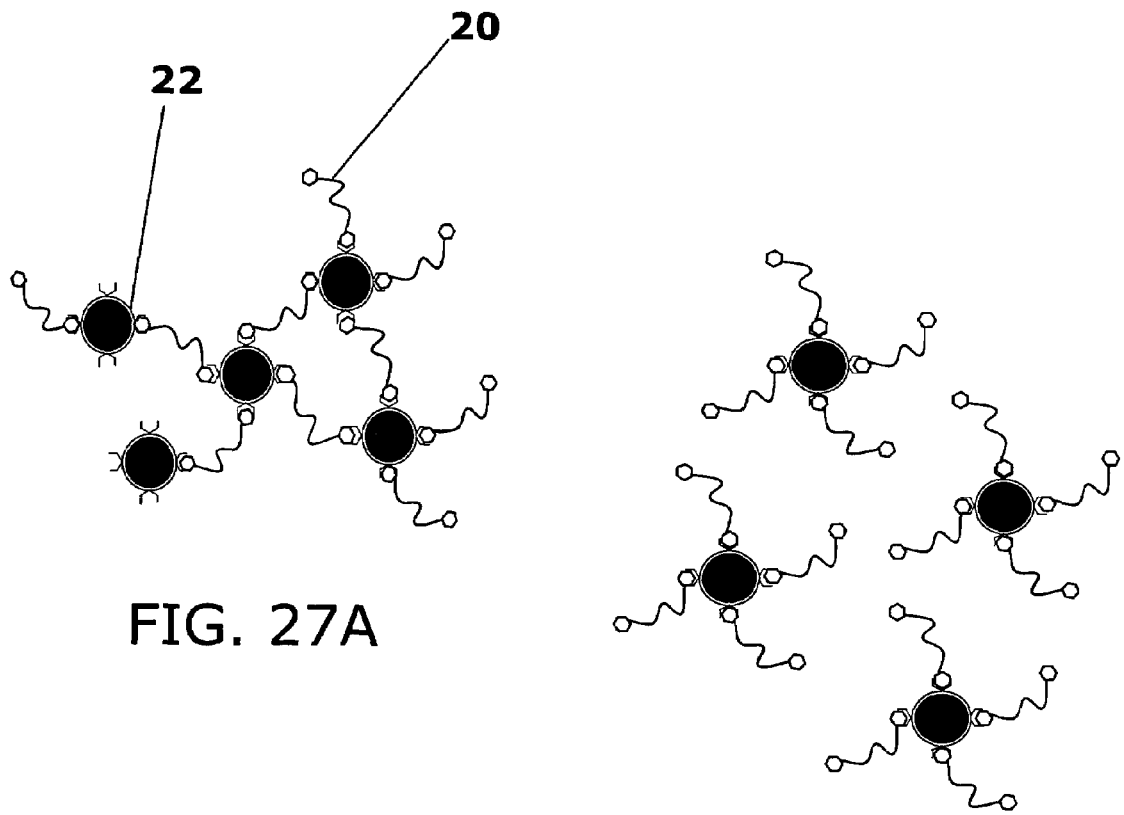
FIG. 27A
FIG. 27B

| Scaffold | Target | Design | Complementary surface sequence* | | | | | | | | |
|---|---|---|---|---|---|---|---|---|---|---|---|
| RBP | | | $9_I$ | $13_I$ | $15_I$ | $16_I$ | $64_I$ | $89_I$ | $90_I$ | $103_H$ | $132_H$ |
| | | WT | S | <u>N</u> | F | F | N | <u>D</u> | <u>R</u> | S | I |
| | Lac | R1(A) | | V | A | R | | <u>S</u> | S | S | |
| GBP | | | $10_I$ | $14_I$ | $16_I$ | $91_I$ | $92_I$ | $152_{II}$ | $154_{II}$ | $158_{II}$ | $183_{II}$ |
| | | WT | Y | <u>D</u> | F | <u>N</u> | K | <u>H</u> | <u>D</u> | <u>R</u> | W |
| | Lac | G1 | K | <u>K</u> | F | <u>K</u> | L | M | H | <u>K</u> | <u>K</u> |
| | | G2 | K | M | K | K | L | <u>K</u> | <u>K</u> | M | <u>K</u> |
| ABP | | | $10_I$ | $11_I$ | $14_I$ | $16_I$ | $17_I$ | $20_I$ | $64_I$ | $89_I$ | $90_I$ |
| | | WT | <u>K</u> | Q | <u>E</u> | W | F | E | C | D | <u>D</u> |
| | Lac | A1 | K | | E | Y | | | A | L | A |
| | | A2 | K | | L | Y | | | A | <u>S</u> | S |
| HBP | | | $11_I$ | $14_I$ | $52_I$ | $70_I$ | $71_I$ | $72_I$ | $77_I$ | $117_{II}$ | $120_{II}$ |
| | | WT | D | Y | L | S | L | <u>S</u> | <u>R</u> | L | T |
| | Lac | H1 | | <u>S</u> | L | S | | <u>K</u> | R | K | S |
| | | H2 | | <u>S</u> | K | T | | <u>K</u> | R | H | S |
| QBP | | | $10_I$ | $13_I$ | $50_I$ | $70_I$ | $75_I$ | $115_{II}$ | $118_{II}$ | $156_{II}$ | $157_{II}$ |
| | | WT | <u>D</u> | F | F | <u>T</u> | <u>R</u> | <u>K</u> | T | <u>H</u> | <u>D</u> |
| | Lac | Q1 | D | L | L | <u>S</u> | <u>R</u> | K | T | H | H |
| | | Q2 | D | <u>R</u> | <u>S</u> | <u>T</u> | <u>R</u> | K | S | H | R |
| | | Q3 | D | L | <u>K</u> | <u>S</u> | <u>D</u> | K | T | H | R |

The Nomenclature for the designed receptors gives the target ligand and a single-letter abbrevation of the scaffold protein.
* Subscripts indicate the location of a residue position: I, N-terminal domain; II, C-terminal domain; H, hinge. Bold letters indicate mutations from wild type (WT) (calculations may predict retention of wild type residues). Underlined letters represent side chains making hydrogen bonds with the ligand (cognate ligand in the case of wild type).

Prior Art

FIG. 36-1

| Scaffold | Target | Design | Complementary surface sequence* | | | | | | | | |
|---|---|---|---|---|---|---|---|---|---|---|---|
| RBP | | | $137_H$ | $141_{II}$ | $164_{II}$ | $190_{II}$ | $214_{II}$ | $215_H$ | $235_{II}$ | | |
| | | WT | A | R | F | N | F | D | Q | | |
| | Lac | R1(A) | K | M | K | I | | S | T | | |
| GBP | | | $211_{II}$ | $236_{II}$ | $256_{II}$ | | | | | | |
| | | WT | N | D | N | | | | | | |
| | Lac | G1 | N | A | D | | | | | | |
| | | G2 | N | A | S | | | | | | |
| ABP | | | $108_{II}$ | $145_{II}$ | $147_{II}$ | $151_{II}$ | $177_{II}$ | $204_{II}$ | $205_{II}$ | $232_{II}$ | $235_{II}$ |
| | | WT | M | L | T | R | N | M | N | N | D |
| | Lac | A1 | A | R | S | S | | I | N | K | |
| | | A2 | A | R | S | S | | I | K | H | |
| HBP | | | $121_{II}$ | $122_{II}$ | $143_{II}$ | $161_{II}$ | | | | | |
| | | WT | T | Q | Q | D | | | | | |
| | Lac | H1 | S | T | | S | | | | | |
| | | H2 | A | T | | I | | | | | |
| QBP | | | $185_{II}$ | | | | | | | | |
| | | WT | Y | | | | | | | | |
| | Lac | Q1 | F | | | | | | | | |
| | | Q2 | F | | | | | | | | |
| | | Q3 | F | | | | | | | | |

The Nomenclature for the designed receptors gives the target ligand and a single-letter abbrevation of the scaffold protein.
* Subscripts indicate the location of a residue position: I, N-terminal domain; II, C-terminal domain; H, hinge. Bold letters indicate mutations from wild type (WT) (calculations may predict retention of wild type residues). Underlined letters represent side chains making hydrogen bonds with the ligand (cognate ligand in the case of wild type).

Prior Art

FIG. 36-2

STIMULI-RESPONSIVE SYSTEMS FOR CONTROLLED DRUG DELIVERY

This application claims the priority of U.S. Provisional Application No. 60/434,076, filed Dec. 17, 2002, the entire contents of which are incorporated herein by reference.

This invention was made with government support under Grant Number CTS-0118705, awarded by The National Science Foundation ("NSF"). The government has certain rights in the invention.

FIELD OF THE INVENTION

This invention pertains to a drug delivery apparatus and method and, more specifically, to a drug delivery apparatus and method in which the rate of drug delivery is determined through a feedback mechanism.

BACKGROUND OF THE INVENTION

Metabolic diseases such as diabetes affect the lives of millions of people. Many of these diseases may be controlled by administration of a particular enzyme, hormone, or other agent. Some of these agents can be ingested as pills or syrups. Others, such as insulin, must be injected daily or even more frequently. Diseases such as diabetes also require constant monitoring of the blood levels of certain molecules. For example, diabetes patients must give themselves multiple finger pricks every day to monitor their glucose levels.

Administration of pills or injected insulin may result in uneven blood concentrations of insulin or other agents over the course of a day. For example, most pills result in a spike in blood concentrations of a drug. These concentrations decrease over time to levels that are not therapeutically effective. In addition, it takes time for agents administered as a pill or even an injection to circulate throughout the body. However, the appropriate levels of metabolic agents or hormones changes over time. Thus, while the average serum levels may be appropriate for the patient, the instant serum concentration of the drug is not optimal at any specific time. As a result, it is desirable to have a drug delivery method that provides a therapeutic agent in the quantities and at the times required by a particular patient.

SUMMARY OF THE INVENTION

In one aspect, the invention is a material for delivery of a therapeutic agent. The material includes a biodegradable polymer functionalized with an indicator analog and a cross-linking agent that cross-links the polymer by interacting with two or more indicator analogs. The therapeutic agent is contained within the polymer. The degradation rate of the polymer depends on the local concentration of the indicator whose analog the polymer is functionalized with, and the material is adapted and constructed to release the therapeutic agent by degrading.

In another aspect, the invention is a method of producing a delivery vehicle for a therapeutic agent. The method includes the steps of forming a reverse microemulsion by adding an aqueous solution to a mixture of a hydrophobic liquid and a surfactant and agitating the mixture. The aqueous solution includes a biodegradable polymer functionalized with an indicator analog, a cross-linking agent that cross-links the polymer by interacting with two or more indicator analogs, and the therapeutic agent. The method further includes causing the cross-linking agent to interact with the polymer to form a cross-linked hydrogel retaining the therapeutic agent therein and separating the hydrogel particles from the remaining components of the reverse microemulsion.

DEFINITIONS

"Biomolecules": The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

"Biocompatible": The term "biocompatible", as used herein is intended to describe materials that do not elicit an undesirable detrimental response in vivo.

"Biodegradable": As used herein, "biodegradable" polymers are polymers that degrade fully (i.e., down to monomeric species) under physiological or endosomal conditions. In some embodiments, the polymers and polymer biodegradation byproducts are biocompatible. Biodegradable polymers are not necessarily hydrolytically degradable and may require enzymatic action to fully degrade.

"Growth Factors": As used herein, "growth factors" are chemicals that regulate cellular metabolic processes, including but not limited to differentiation, proliferation, synthesis of various cellular products, and other metabolic activities. Growth factors may include several families of chemicals, including but not limited to cytokines, eicosanoids, and differentiation factors.

"Polysaccharide", "carbohydrate" or "oligosaccharide": The terms "polysaccharide", "carbohydrate", or "oligosaccharide" refer to a polymer of sugars. The terms "polysaccharide", "carbohydrate", and "oligosaccharide", may be used interchangeably. Typically, a polysaccharide comprises at least three sugars. The polymer may include natural sugars (e.g., glucose, fructose, galactose, mannose, arabinose, ribose, and xylose) and/or modified sugars (e.g., 2'-fluororibose, 2'-deoxyribose, and hexose).

"Small molecule": As used herein, the term "small molecule" is used to refer to molecules, whether naturally-occurring or artificially created (e.g., via chemical synthesis), that have a relatively low molecular weight. Typically, small molecules are monomeric and have a molecular weight of less than about 1500 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered acceptable for use in accordance with the present invention.

"Bioactive agents": As used herein, "bioactive agents" is used to refer to compounds or entities that alter, inhibit, activate, or otherwise affect biological or chemical events. For example, bioactive agents may include, but are not limited to, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anti-coagulants and/or anti-thrombotic agents, local anesthetics, ophthalmics, prostaglandins, anti-depressants, anti-psychotic substances, anti-emetics, and imaging agents. In certain embodiments, the bioactive agent is a drug.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmcopeial Convention, Inc., Rockville Md., 2001, all of which are incorporated herein by reference.

BRIEF DESCRIPTION OF THE DRAWING

The invention is described with reference to the several figures of the drawing, in which, FIG. 1A is a schematic of a mechanism of degradation of a cross-linked polymer according to an embodiment of the invention.

FIG. 1B is a schematic of an alternative mechanism of degradation of a cross-linked polymer according to an embodiment of the invention.

FIG. 1C is a schematic of a cross-linked polymer according to an alternative embodiment of the invention.

FIG. 26 is a sugar-responsive particle dissolution surface for particles synthesized in 0.100 ml aqueous phase dispersed in 1.9 g of oil and surfactants (FITC-dex MW=42K and [A]$_{aq}$=50 mg/ml).

FIG. 27A is a schematic illustrating the interaction of dextran and Con A given an excess of Con A.

FIG. 27B is a schematic illustrating the interaction of dextran and Con A given an excess of dextran.

FIG. 36 is a table adapted from Looger, et al. *Nature*, 423, 185-190 (2003) illustrating the modifications to wild type binding proteins for ribose (RBP), glucose (GBP), arabinose (ABP), histidine (HBP), and glutamine (QBP) to create binding sites for L-lactate.

DETAILED DESCRIPTION OF CERTAIN PREFERRED EMBODIMENTS

Figure 2:
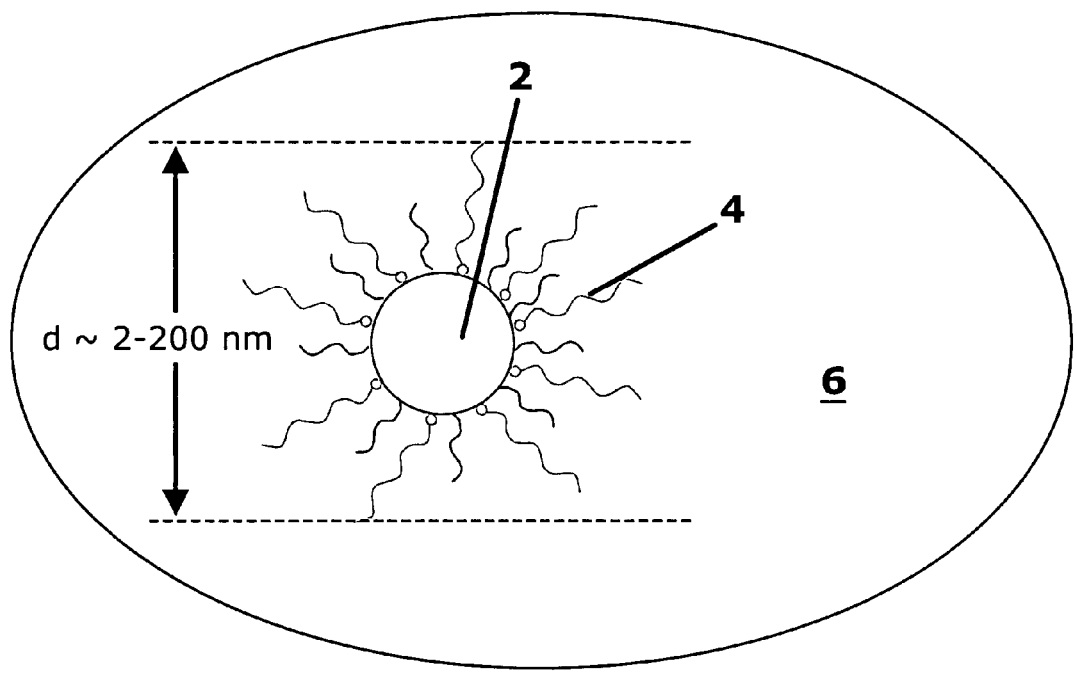
FIG. 2 is schematic diagram of a reverse microemulsion for use with techniques provided by the invention.

In one embodiment, the invention is a material for delivery of a therapeutic agent. The therapeutic agent may be a bioactive agent, small molecule, or biomolecule. The material includes a biodegradable polymer functionalized with an indicator analog and a cross-linking agent that cross-links the biodegradable polymer by interacting with two or more indicator analogs. The therapeutic agent is contained within the cross-linked polymer. The degradation rate of the cross-linked polymer depends on the local concentration of the indicator whose analog the biodegradable polymer is functionalized with, and the material is adapted and constructed to release the therapeutic agent by degrading.

In another embodiment, the invention is a method of producing a delivery vehicle for a therapeutic agent. The method includes the steps of forming a reverse microemulsion by adding an aqueous solution to a mixture of a hydrophobic liquid and a surfactant and agitating the mixture. The aqueous solution includes a biodegradable polymer functionalized with an indicator analog, a cross-linking agent that cross-links the polymer by interacting with two or more indicator analogs, and the therapeutic agent. The method further includes causing the cross-linking agent to interact with the biodegradable polymer to form a cross-linked hydrogel retaining the therapeutic agent therein and separating the hydrogel particles from the remaining components of the reverse microemulsion.

In still another embodiment, the invention provides a cross-linked polymer whose degradation rate is determined by environmental levels of a particular indicator. That is, as the local concentration of the indicator increases, the degradation rate of the cross-linked polymer increases, and vice versa. While cross-linked, the cross-linked polymer encapsulates a particular therapeutic agent, which agent is released as the cross-linked polymer degrades. Thus, the release rate of the therapeutic agent increases as the increased level of the indicator causes the cross-linked polymer to degrade more quickly. Once the local concentration of the indicator decreases, degradation slows. The therapeutic agent may be encapsulated by the cross-linked polymer. For example, the cross-linked polymer may be formed as a hydrogel having pores that are too small to allow diffusion of the therapeutic agent out of the cross-linked polymer before it degrades. Alternatively, the therapeutic agent may be covalently or non-covalently linked to the polymer. The polymer is cross-linked by the interaction of indicator analogs and cross-link receptors in the polymer. As used herein, the term "indicator analog" indicates a chemical group that interacts with a cross-link receptor in the same manner as the corresponding indicator.

One skilled in the art will recognize that the indicator analog may have essentially the same composition as the indicator itself or may be a chemically related species. Where the affinity of the cross-link receptor for the indicator and the indicator analog are different, the density of cross-links should be modified so the desired amount of the therapeutic agent is released for a given local concentration of indicator. The indicator analog may be incorporated into the polymer chain during polymerization as part of the backbone or as a side group. For example, the polymer chain may be functionalized with the indicator analog. Alternatively, a polymer chain may be derivatized with the indicator analog post-polymerization so that the indicator analog is a species linked to the polymer chain through its backbone or side groups, if any.

In one embodiment, the polymer is cross-linked by a polyfunctional cross-linking agent including cross-link receptors (FIG. 1, anchored "v") that reversibly interact with the indicator analogs on the polymer chain. As the local concentration of the indicator (diamond) increases, it competes with the indicator analog (anchored diamond) to interact with the cross-linking receptor, eventually detaching the polyfunctional cross-linking agent from the polymer and de-cross-linking the polymer (FIG. 1A). One skilled in the art will recognize that the indicator analog may be part of the polyfunctional molecule and that the cross-link receptors may be incorporated into the polymer chain in the same manner as described above for the indicator analog (FIG. 1B).

The polyfunctional molecule may be covalently linked to the polymer chain while still cross-linking the polymer through one or more non-covalent interactions between the indicator analogs and the cross-link receptors (FIG. 1C). Non-covalent interactions may include ligand-receptor interactions, chemical adsorption, electrostatic interactions, ionic bonding, hydrogen bonding, van der Waals interactions, hydrophobic interactions, dipole-dipole interactions. A variety of ligand-receptor interactions may be exploited for use with the invention. For example, the cross-link receptor may interact with the indicator analog through an antibody-antigen interaction. In one embodiment, the cross-link receptor is either the antibody or the antigen, and the indicator analog includes the other. Biotin and strepavadin may be exploited in the same manner. Other ligand-receptor pairs that may be exploited for use with the invention include, but are not limited to, folate/folate binding protein and iron/lactoferrin.

The techniques of the invention may be exploited to manipulate feedback mechanisms. In one embodiment, a patient outcome is traced to an excess of a particular substance. A receptor for that substance is adapted for use as a cross-link receptor. For example, the receptor may simply be attached to a biodegradable polymer to form a cross-linking agent. A polymer including the characteristic chemical groups of the substance is selected for use as an indicator analog, or the substance itself is attached to a biodegradable polymer. The polymer including the indicator analog is cross-linked with the cross-linking agent in the presence of a therapeutic agent that causes a reduction in the level of the substance in the patient. For example, blood glucose levels may be used to control the release of insulin from a drug delivery vehicle formed by cross-linking a polysaccharide (the indicator analog for glucose) with a lectin, which typically binds glucose and other sugars. Other molecules that act to lower blood glucose levels by stimulating insulin secretion in Type 2 diabetics include but are not limited to sulfonylureas, glucagon-like peptide-1 (GLP-1), and GLP-1 analogues such as exanitide, obtained from the Gila monster.

In a second embodiment, the indicator analog and the cross-link receptor are not related metabolically to the function of the therapeutic agent. That is, the cross-linked polymer degrades in the presence of the indicator to release a therapeutic agent with a different function. For example, the techniques provided by the invention may be used to provide long-term, mealtime dosing of bioactive agents such as antibiotics and anticancer drugs. Agents to lower lipid levels, for example, lovastatin, attorvastatin, or simvastatin, or triglyceride levels, for example, gemfibrozil, may also be encapsulated using the teachings of the invention and released at mealtimes. To deliver a biomolecule, bioactive agent or small molecule using mealtime dosing, it need simply be substituted for insulin in a glucose-responsive drug delivery device. The increase in serum glucose causes the cross-linked polymer to degrade, releasing the therapeutic agent without significantly changing the local glucose concentration.

Suitable biodegradable polymers for use in the practice of the invention are well known in the art and include poly(lactic acid) (PLA), poly(glycolic acid) (PGA) and PLA-PGA co-polymers (PLGA). Additional biodegradable materials include poly(anhydrides), poly(hydroxy acids), poly(ortho esters), poly(propylfumerates), poly(caprolactones), polyamides, polyamino acids, polyacetals, biodegradable polycyanoacrylates, biodegradable polyurethanes and polysaccharides. Natural polymers including alginate, collagen-glycosaminoglycan, collagen, dextran, pullulan, mannan, and chitosan may also be exploited for use with the invention.

Polymers including various pendant groups may also be employed. Such pendant groups may be used to attach therapeutic agents, cross-link receptors, or indicator analogs to the polymers. For example, polymers having —COOH pendant groups (carboxyl bearing polymers, or CBPs) may be used with the invention. Such polymers may naturally include carboxyl groups or may be modified to include them. Exemplary CBPs include but are not limited to carboxylated polysaccharides (CPS) such as alginate (Ag), carboxymethylated-D-manno-D-glucan (CMMG, available from Daiichi Pharmaceutical Co.), carboxymethyldextran (CMDex), carboxymethylchitin (CMCh, available from Katakura Chikkalin Co.), N-desulfated N-acetylated heparin (DSH), and hyaluronic acid (HA). DSH and CMDex may be synthesized according to Sugahara, et al., *Biol. Pharm. Bull.*, 24, 535-543 (2001) (see examples). In general, hydroxylated polymers may be carboxylated through reaction with chloroacetic acid under basic conditions. The degree of COOH substitution with respect to monomer may vary between 1 and 100 mol %. Naturally occuring carboxylated polymers include but are not limited to carboxylated poly (amino acids) (CPAA) such as poly-L-glutamate and poly-L-aspartate. The carboxylate content may be varied between 1 and 100% mol COOH/mol AA residue by copolymerizing carboxylated amino acids (e.g., amino acids with a carboxyl group in addition to the carboxyl group which becomes part of the polymer backbone) with non-carboxylated amino acids (e.g., amino acids whose only carboxyl group becomes part of the polymer backbone).

In another embodiment, polymers having —$NH_2$ pendant groups (—$NH_2$ bearing polymers, or NBP) may be used with the invention. Such polymers may be naturally occurring or may be chemically modified to include a primary amine. The latter include but are not limited to —$NH_2$ pendant polysaccharides (NPS) such as deacetylated chitosan (Ch) (Sigma Aldrich, Milwaukee, Wis.) and diethylaminoethyl ether dextran (DEAEDex), MW 500,000 g/mol (Polysciences, Warrington, Pa.). The degree of —$NH_2$ substitution with respect to monomer may vary between 1 and 100 mol %. Naturally occuring aminated polymers include but are not limited to poly(amino acids) such as poly-L-lysine (PLL) and its enantiomer. The amine content may be varied between 1 and 100% mol $NH_2$/mol AA residue by copolymerizing an aminated amino acid (e.g., an amino acid with an amine in addition to the amine group that eventually becomes part of the polymer backbone) with non-aminated amino acids (e.g., an amino acid whose only amine is that which eventually becomes part of the polymer backbone). Proteins including epsilon-$NH_2$ lysine groups (and which naturally have alpha-$NH_2$ terminal groups) may also be used with the invention.

In another embodiment, polymers having —OH pendant groups (—OH bearing polymers, or OBP) may be used with the invention. Such polymers may be naturaly hydroxylated or may be chemically modified using standard organic chemistry techniques to include a hydroxyl group. In addition to dextran, naturally occurring OBP include but are not limited to polysaccharides such as yeast mannan (Mn), pullulan (Pl), amylose (Am), amylopectin (AmP), glycogen (Gl), cellulose (Cl), hyaluronate (Hy), chondroitin (ChD), and dextran (Dx), all of which may be obtained commercially from Sigma Aldrich. In addition, poly (amino acids) such as poly(serine), poly(threonine), poly(tyrosine), and poly(4-hydroxyproline) may also be employed as hydroxylated polymers. The hydroxyl content of the poly(amino acids) may be varied between 1 and 100% mol —OH/mol AA residue by co-polymerizing hydroxylated amino acids with non-hydroxylated amino acids. Of course, carboxyl, amino, and hydroxyl pendant groups may be mixed in a single polymer by co-polymerizing the appropriate amino acids in desired ratios.

Co-polymers, mixtures, and adducts of the above polymers may also be used in the practice of the invention. Indeed, such combinations may be particularly useful for optimizing the mechanical and chemical properties of the matrix. Both the choice of polymer and the ratio of polymers in a co-polymer may be adjusted to optimize the stiffness of the matrix and the degradation rate of both the cross-linked polymer and the component biodegradable polymer.

Exemplary polyfunctional molecules for use as cross-linking agents include plant lectins, or phytohemoagglutinins (PHAs), such as concanavalin A (Con A) and those derived from *pisum sativum* (pea), *lathyrus odoratus* (sweet pea), *lens culinaris* (lentil), *narcissus pseudonarcissus* (daffodil), *vicia faba* (fava bean), and *vicia sativa* (garden vetch) as well as human analogues such as human mannan binding protein (MBP, also called mannan binding lectin, Sheriff, et al., *Structural Biology*, 1, 789-794 (1994); Dumestre-Perard, et al., *Molecular Immunology*, 39, 465-473 (2002)), human pulmonary surfactant protein A (SP-A, Allen, et al., *Infection and Immunity*, 67, 4563-4569 (1999)), human pulmonary surfactant protein D (SP-D, Persson, et al., *The Journal of Biological Chemistry*, 265, 5755-5760 (1990)), CL-43 (a human serum protein), and conglutinin. One skilled in the art will recognize that any polyfunctional binding protein may be exploited for use with the invention.

Other polyfunctional molecules may be constructed by chemically linking multiple monofunctional binding proteins, for example, antibodies, cell membrane receptors, and enzymes. Still other polyfunctional molecules may be constructed by chemically linking specific binding fragments of proteins, for example, antibodies, cell membrane receptors, lectins, collectins, and enzymes. Exemplary protein fragments include truncated MBP (Eda, et al., *Biosci. Biotechnol. Biochem.*, 62, 1326-1331 (1998)), truncated conglutinin (S. Eda, et al. Biochem. J. 316, 43 (1996)), truncated SP-D (S. Eda, et al. Biochem. J. 323, 393 (1997)), and the glucose/galactose binding protein of *E. Coli* (Salins, et al., *Analytical Biochemistry*, 294, 19-26 (2001)). In addition, a variety of monovalent ligand-binding proteins are available commercially from Sigma-Aldrich, including folate-binding protein, thyroxine-binding globulin, and lactoferrin.

Monofunctional molecules and fragments may be linked directly to one another or to polymer scaffolds. Suitable scaffold materials include but are not limited to the CBP's, NBP's, and OBP's described above. Proteins may be attached to these polymers using the insulin-conjugation procedures described below. In general, the pendant groups on CBP, NBP, and OBP may be used to attach a variety of indicator analogs or cross-link receptors using standard organic chemistry reactions (see March, "Advanced Organic Chemistry", 5th ed. John Wiley and Sons, New York, N.Y., 2001, incorporated herein by reference) to form polyfunctional cross-linking agents.

For example, iron-dextran may be purchased commercially from Sigma-Aldrich and condensed with polyfunctional lactoferrin to encapsulate deferoxamine, which may be used in treating iron overload disorders. Thyroxine-$NH_2$ may be conjugated to OBP's using the CNBr synthesis described in Example 18. Thyroxine-NBP is then condensed with polyfunctional thyroxine-binding globulin to produce a thyroxine-responsive delivery system for treating thyroid disorders. For example, methimazole and propylthiouracil may be encapsulated in a thyroxine-responsive delivery system to treat hyperthyroidism. In addition, folate may be bound to NBP's using carbodiimide coupling as described above for CBPs and sugar. Folate-NBP is then condensed with polyfunctional folate-binding protein to produce a folate-responsive delivery system.

Any of these cross-linking agents may be chemically modified with short-chain polymers, for example, polyethyleneglycol (PEG), to reduce in vivo immunogenic response. Activatyed $PEG_2$, or 2,4-Bis[O-methoxypoly(ethylene glycol)]-6-chloro-s-triazine is synthesized according to K. Ono, et al., *J. Biomater. Sci. Polymer Edn.* 2, 61 (1991). Briefly, 110 mg of monomethoxypolyethylene glycol is dissolved in 500 ml of anhydrous benzene. The solution is refluxed at 80° C. in the presence of 25 g of molecular sieves 4 A (powder) for 6 h. After cooling, 50 g of zinc oxide and 1.85 g of cyanuric chloride are added at room temperature. After refluxing at 80° C. for 53 h, the resulting mixture is cooled to room temperature, diluted with 500 ml of benzene and filtered. The filtrate is evaporated to dryness under reduced pressure to give activated $PEG_2$.

PEGylation may be performed according to T. Ueno, et al., *J. Biomater. Sci. Polymer Edn.* 7, 753 (1996). To 0.4 ml of protein (2.5 mg/ml), dissolved in 0.5 M borate buffer (pH 10.0), 1-100 mg of activated $PEG_2$ is added. The mixture is stirred at 37° C. for 1 h to complete the reaction: amino groups in lysine residues and N-terminal amino groups are modified with activated $PEG_2$ to form PEG-protein.

In another embodiment, PEGylation is carried out as follows (J. J. Kim and K. Park, *Pharmaceutical Research* 18, 794 (2001)). 100 mg of protein is dissolved in 10 ml of 0.1 M borate buffer, pH 8.5, and the solution is kept in an ice bath. Monomethoxy poly(ethylene glycol) p-nitrophenyl carbonate (MPEG-NPC) is slowly added to the protein solution at varying concentrations to modify the degree of PEGylation. The temperature is then gradually increased from 4° C. to room temperature, and the solution allowed to react for 20 hours. The resulting solution is dialyzed exhaustively against deionized water and lyophilized to obtain purified PEG-protein.

To encapsulate the therapeutic agent in a cross-linked polymer, a solution of an appropriate cross-linking agent may be added to a solution of the desired biodegradable polymer and therapeutic agent under conditions to allow the cross-linking agent to interact with the polymer. The interaction cross-links the polymer, encapsulating the therapeutic agent. In an alternative embodiment, the therapeutic agent is covalently or non-covalently linked to the biodegradable polymer. The biodegradable polymer and the cross-linking agent may include one or the other of an indicator analog and its corresponding cross-link receptor.

One skilled in the art can easily optimize the cross-linking conditions through routine experimentation. For example, an excess of divalent ions such as calcium and magnesium promote the cross-linking of dextran by plant lectins. Calcium alone is typically sufficient to promote cross-linking with mammalian lectins, but higher concentrations are generally needed. The optimal concentration of divalent ion may be determined by producing gels with various concentrations of calcium and/or magnesium. Likewise, the cross-linking efficiency and indicator sensitivity of the gel may be optimized by using the techniques described in Example 1.

For example, the optimal concentration of PHA or an artificial multimeric glucose binding protein may be determined by adding a concentrated solution of PHA containing 1 mM to 100 mM of calcium to each of several solutions containing varying concentrations of dextran or other biocompatible polymer. Alternatively, insulin-polysaccharide conjugates or insulin-polymer conjugates containing glucose or mannose residues may be combined with the cross-linking agent. The cross-linking efficiency and glucose sensitivity of the gels may then be determined as described in Example 1. The insulin release may be monitored as described in Example 3. One skilled in the art will recognize that the same techniques may be used to determine the cross-linking efficiency, indicator sensitivity, and therapeutic agent release of other gels produced using the techniques of the invention.

In one embodiment, the cross-linked polymer is an insoluble hydrogel. The hydrogel only degrades as competition from the indicator with the interaction between the cross-linking agent and the indicator analog interrupts the cross-links. The hydrogel degrades in a layer-by-layer fashion from the outside in, allowing the therapeutic agent to be released at an approximately constant rate as the hydrogel degrades. The hydrogel may be implanted at a site in a patient, where it will deliver the therapeutic agent at a relatively constant rate with respect to the local level of the indicator.

Such a material is optimal for one-time therapies, for example, after surgery. The hydrogel degrades completely as the therapeutic agent is delivered, obviating a second surgical procedure to remove the drug delivery device. Alternatively, the material may be injected into a patient. Even where a patient requires long term treatment, the degradation mechanism of the drug delivery material can reduce the frequency of injections by preventing the therapeutic agent from being wasted. The agent is only released as needed, not constantly.

Alternatively, the cross-linked polymer may be fabricated as a mass of nanoparticles through a reverse microemulsion (RM). RMs are spontaneously forming, thermodynamically stable, dispersed systems having a uniform particle size in the range of 2-200 nm (FIG. 2). In general, an aqueous core 2 is stabilized by a non-ionic surfactant 4 in a continuous oil phase 6. These structural characteristics make RM's an ideal medium for the controlled synthesis of ultrafine particles. Because the resulting nanoparticles will be used for drug delivery applications, it is highly desirable to construct these systems with biocompatible surfactants and oils. Such systems constructed from soybean and sunflower seed oils, as well as food-grade surfactants such as sorbitan esters and ethoxylated fatty esters, have been characterized by several researchers (P. P. Constantinides, et al., *Pharm. Res.* 11, 1385 (1994)). Appropriate oils include soybean oil, (Sigma-Aldrich), Arlacel 186, (a mixture of mono and diglycerides of fat-forming fatty acids available from ICI Surfactants), Captex 355 (a mixture of triglycerides of caprylic and capric acids available from Abitec Corporation), Capmul MCM, (a mixture of mono-diglycerides of medium chain caprylic and capric fatty acids available from Abitec Corporation), Myvacet (a mixture of acetylated monoglycerides available from Eastman Chemical Company), and Myverol 18-92 (a monoglyceride produced from canola oil available from Eastman Chemical Company). Combinations of these oils may be used to optimize the composition of the RM. Exemplary surfactants include Tween 80 (polyoxyethylene 20-sorbitan monooleate, available from ICI Surfactants), Span 80 (sorbitan monooleate, available from ICI Surfactants), and Cremophor EL (ethoxylated high purity castor oil available from BASF Corporation). The RM should be optimized to prevent the development of large droplets, e.g., larger than about 500 nm.

The procedure for synthesizing RMs depends in part on the stability of RMs in the presence of the encapsulated materials. In general, the polymer, cross-linking agent, and therapeutic agent are combined in the aqueous phase under conditions that minimize cross-linking. The aqueous phase is then combined with a mixture of surfactant and oil. The emulsion is treated to favor the interaction between the polymer chains and the cross-linking agent, causing the polymer chains to cross-link within and around the aqueous domains. For example, the pH may be adjusted or the temperature changed. Some time may be allowed for the particles to form, after which the particles are separated from the media, for example, by centrifugation, and washed in a hydrogen-bonding solvent such as ethanol. The separation and rinsing steps may be repeated several times to ensure complete removal of oil and surfactant. The particles are then washed with aqueous buffer to remove uncross-linked polymer chains and loosely encapsulated therapeutic agent and dried. One skilled in the art will recognize that composition, temperature, and the choice of RM system may all be optimized to achieve a desired particle size and morphology.

Figure 3:
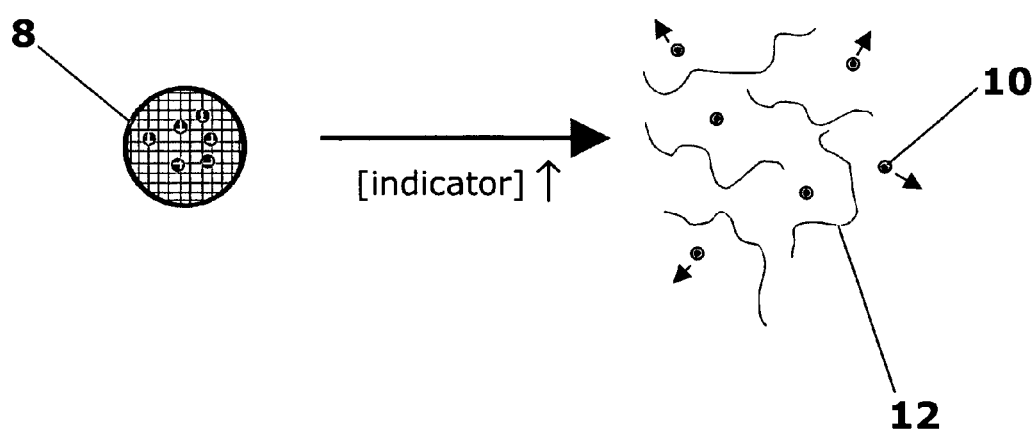
FIG. 3 is a schematic illustrating the release of a therapeutic agent according to an embodiment of the invention.

Particles formed in RMs may be used to deliver the therapeutic agent through injection, ingestion, or inhalation. As a result, these materials are useful for repeated administration of the therapeutic agent. For example, oral or ingestable insulin would reduce the number of injections required by diabetics and provide insulin in quantities more closely related to the metabolic cycle of the patient. The nanoparticle 8 degrades to release the therapeutic agent 10, and the now uncross-linked polymer chains 12 are degraded hydrolytically or enzymatically (FIG. 3). Particle size may be optimized depending on the delivery vehicle, desired residence time, and other factors. In some applications, particles having a size of about 100 m to 300 nm or 300 nm to 500 nm may be employed.

Figure 15:
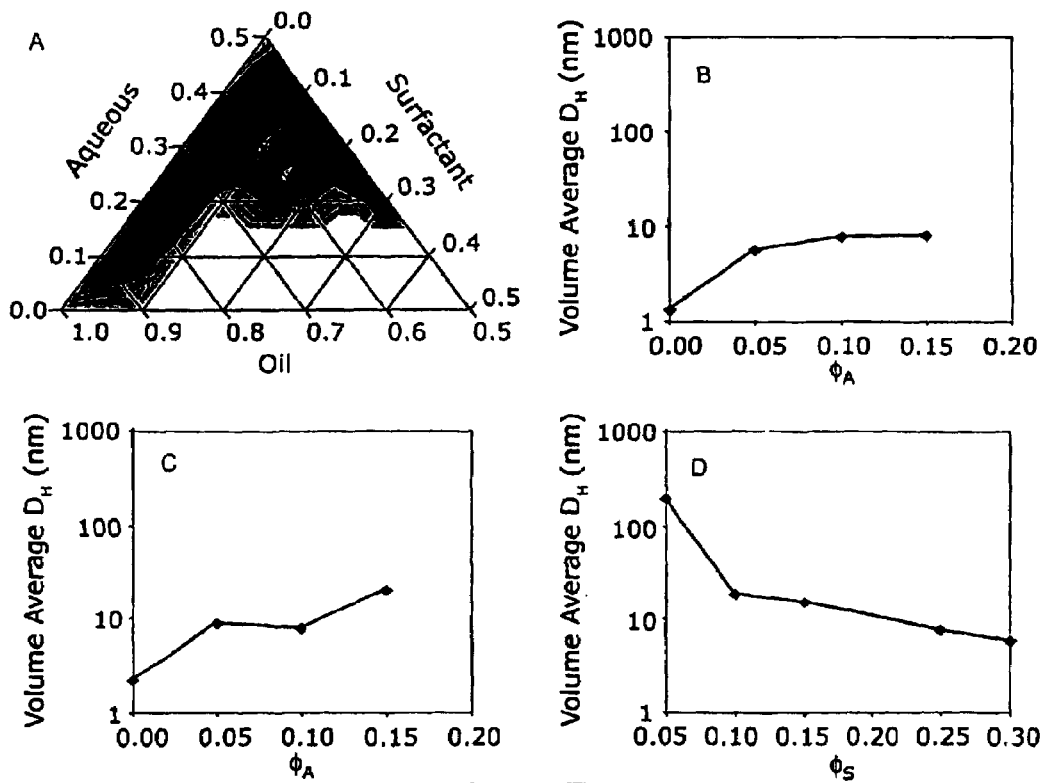
FIG. 15A is a ternary phase diagram for a mixture of 3:2 w/w Tween 80/Span 80 and 3:1 w/w Captext 355/Capmul MCM with water.
FIGS. 15B-D illustrate dynamic light scattering (DLS) results for select pseudoternary compositions as a function of water volume fraction ($\Phi_A$) at (A) constant surfactant volume fraction ($\Phi_S$=0.25) and (B) constant oil volume fraction ($\Phi_O$=0.65), and (C) as a function of surfactant volume fraction ($\Phi_S$) at constant water volume fraction ($\Phi_A$=0.10)
Figure 18A:
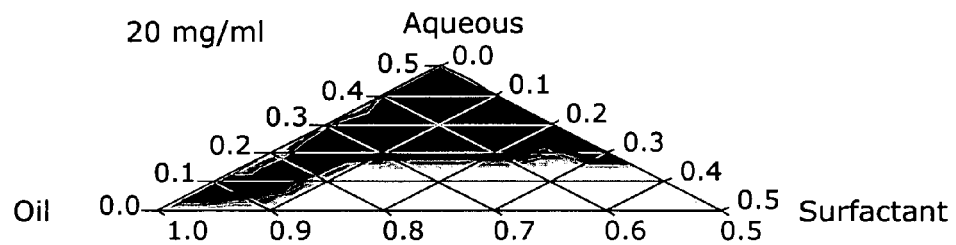
FIG. 18 is a series of ternary phase diagrams illustrating the concentration dependent of dissolved insulin on reverse microemulsion phase behavior ([insulin]$_{aq}$=(A) 20, (B) 10, and (C) 5 mg/ml).
Figure 18B:
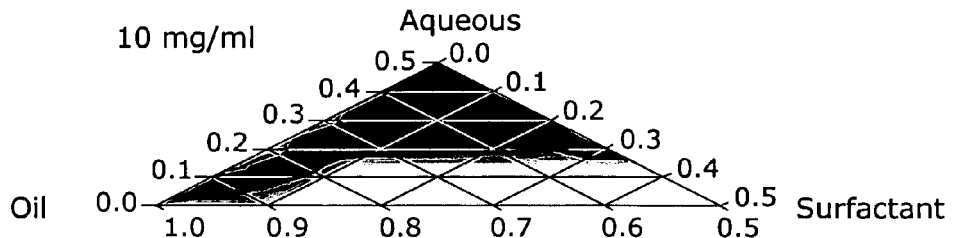
Figure 18C:
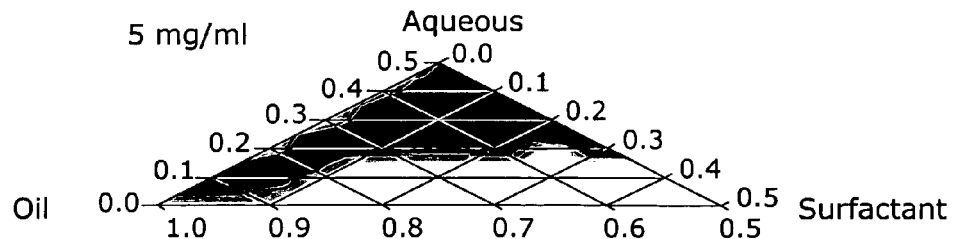
Figure 19A:
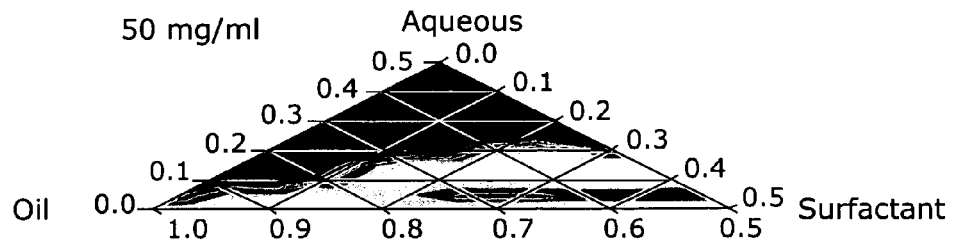
FIG. 19 is a series of ternary phase diagrams illustrating the concentration dependents of dissolved Con A on reverse microemulsion phase behavior ([Con A]$_{aq}$=(A) 50, (B) 25, and (C) 12.5 mg/ml).
Figure 19B:
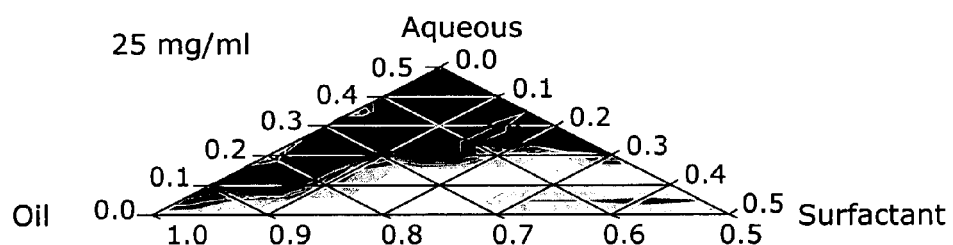
Figure 19C:
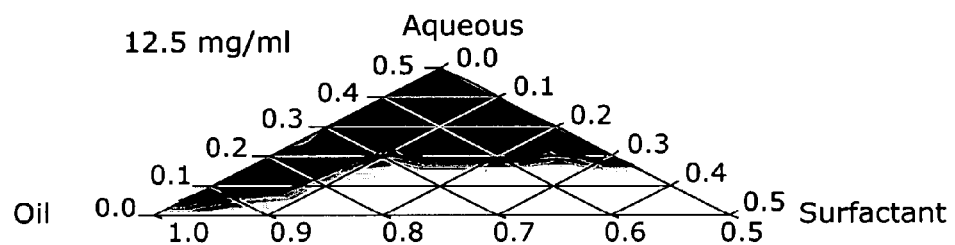

Alternatively, coarse emulsions may be used to produce larger particles. Smaller amounts of surfactant are employed and the solutions are mixed to promote the formation of droplets. FIGS. 15A, 18, and 19 all depict compositions where larger particles are formed, as evidenced by the cloudiness of the mixture of oil, water, and surfactant. In some embodiments, particles may have a size of, for example, 500 nm to 5 µm, 5 µm to 50 µm, 50 µm to 100 µm, or even larger.

Stimuli-responsive particles may be synthesized in aqueous solution through self assembly. In one embodiment, the therapeutic agent is attached to the biocompatible polymer. Because the biocompatible polymer-therapeutic agent complex associates through affinity binding with the cross-linking agent, there is less need for reaction compartmentalization as described in the RM synthesis. In general, a solution containing the cross-linking agent is combined with a second solution containing the biocompatible polymer-therapeutic agent under conditions to promote cross-linking. In one example, a Con A solution at 10 mg/ml in a 20 mM pH 7.0 BES buffer containing 1 mM $Ca^{2+}$, 1 mM $Mn^{2+}$, and 1 M NaCl was combined with a dextran-insulin solution at 1 mg/ml in a 20 mM pH 7.0 BES buffer containing 150 mM NaCl. Precipitated particles formed within minutes that were centrifuged, washed repeatedly, and freeze-dried to obtain a powder. The powder was dissolved in buffered saline solutions containing glucose at concentrations varying between 50 and 500 mg/dl. The resulting insulin-dextran dissolution from the particles increased with increasing glucose concentration in a manner similar to the gels and RM-derived nanoparticles. This procedure is easily performed aseptically and does not require large amounts of oil and surfactants to carry out.

Fluorophores such as fluorescein isothiocyanate (FITC), tetramethylrhodamine isothiocyanate (TRITC), and rhodamine isothiocyanate (RITC) may be used with the drug delivery vehicles of the invention. One skilled in the ar will recognize that other biocompatible fluorophores may also be employed. For example, a fluorophore may be linked to the biodegradable polymer or cross-linking agent or encapsulated in the cross-linked polymer. For a cross-linked polymer delivered subcutaneously, fluorescence spectroscopy using standard clinical autofluorescence techniques may be used to determine the amount of cross-linked polymer still present and whether the patient needs a new dose. In general, a light source and a detector are disposed on a patient, for example, on a finger or arm. The light source excites luminescence of a particular species in the body, which is then detected. Autofluorescence techniques may also be used to determine the amount of the therapeutic agent that has been released in the blood. The fluorophore and the therapeutic agent are released together, and the amount of one can be correlated to serum levels of the other. Alternatively, the fluorophore may be cleared by the kidneys, and fluorescent measurements of urine may be used to determine either how much therapeutic agent has been released or simply whether the cross-linked polymers have completely degraded.

In one embodiment, self-quenching fluorophores are used in the cross-linked polymer. Both the biocompatible polymer and the cross-linking agent are labeled with fluorophores. The photon emitted by one fluorophore is absorbed by the other, with non-luminescent relaxation. As the cross-linked polymer degrades, the biocompatible polymer and the cross-linking agent are separated, allowing the photon to be detected externally instead of quenched.

Fluorophores may also be used to facilitate pharmacokinetic studies. The rate with which a therapeutic agent is transported from a subcutaneous or intramuscular site to another site in the body may be measured by measuring the fluorescence of an agent released from the cross-linked polymer along with the therapeutic agent. Alternatively, the fluorophore may be used to determine the rate of in vivo degradation and how that rate changes as the volume of the cross-linked polymer changes. A fluorophore linked to the therapeutic agent can also help determine the rate of non-stimuli responsive leakage from the cross-linked polymer.

EXAMPLE 1

Glucose-Sensitive Hydrogels for Delivery of Insulin

Material Selection

Con A, a lectin derived from the jack bean plant, was initially chosen as the glucose-binding protein because it is inexpensive, readily available, and extensive work has already been done to evaluate its sugar binding properties. Con A-derived systems represent a tractable model for development of insulin-delivery vehicles employing alternative sugar-binding proteins such as human mannan binding lectin (MBL).

Because the end application requires repeated dosage, the biodegradable polymer is preferably biocompatible and biodegradable to avoid potentially harmful accumulation. Dextran, poly(α-D-glucose), is attractive because it binds Con A, is available at molecular weights ranging from 2K to 2000K, and is already FDA approved for use as a blood plasma volume expander. Dextran is also a versatile molecule, capable of being covalently modified at the free —OH groups with a variety of chemicals, drugs, and proteins (R. Mehvar, *J. Control. Release* 69, 1 (2000)). For example, conjugation with fluorescein isothiocyanate (FITC-Dex) permits independent analysis of the efficiency of particle cross-linking and glucose sensitive dissolution. As detailed below, we exploited three exemplary modifications: (1) fluorescent labeling, (2) glycosylation, and (3) drug conjugation.

Gel Synthesis and Characterization

Previous attempts at forming glucose-sensitive gels from dextrans and other polysaccharides have resulted in extraordinarily slow responses to physiological glucose concentrations, an inability to tune the glucose response, and non-specific insulin leakage from the gels. (J. J. Kim, K. Park, *J. Control. Release* 77, 39 (2001); S. Tanna, et al., *J. Pharm. Pharmacol.* 11, 1461 (2002)) In addition, due to the more viscous than plastic nature of the gels, they could not be readily isolated to measure their insulin release properties. We have discovered a set of material parameters and synthesis conditions that result in gels of Con A and dextran with superior glucose response and mechanical stability than those previously synthesized.

For each experiment, 0.100 ml of Con A, dissolved at 100 mg/ml in 20 mM BES buffered saline containing 1 mM $Mn^{2+}$, 1 mM $Ca^{2+}$, and 1 M NaCl, was added to 0.100 ml of a dextran solution, dissolved at a known concentration in 20 mM BES buffered saline containing 150 mM NaCl. The solutions were allowed to react for one hour, after which the resulting gels were separated from the supernatant. The gels were washed twice with 1 ml of BES buffered saline solution and freeze-dried. To evaluate the amount of dextran participating in the gel reaction as a function of dextran molecular weight (MW) and Con A/dextran ratio, the dextrans were fluorescently labeled to easily detect their concentration in solution (MW 70 K and 170 K labeled with tetramethylrhodamine isothiocyanate (TRITC), MW 280 K and 500 K labeled with fluorescein isothiocyanate (FITC)). The fluorescence of in each of the supernatants was measured using a Molecular Devices fmax fluorescence spectrophotometer (TRITC: $\lambda_{ex}$=544 mm, $\lambda_{em}$=590 nm; FITC: $\lambda_{ex}$=485 mm, $\lambda_{em}$=538 nm), and converted to concentrations using a set of standard curves.

$$X_{CL} = \frac{[\text{dextran}]_{total} - [\text{dextran}]_{supernatant}}{[\text{dextran}]_{total}} \quad (1)$$

Figure 4:
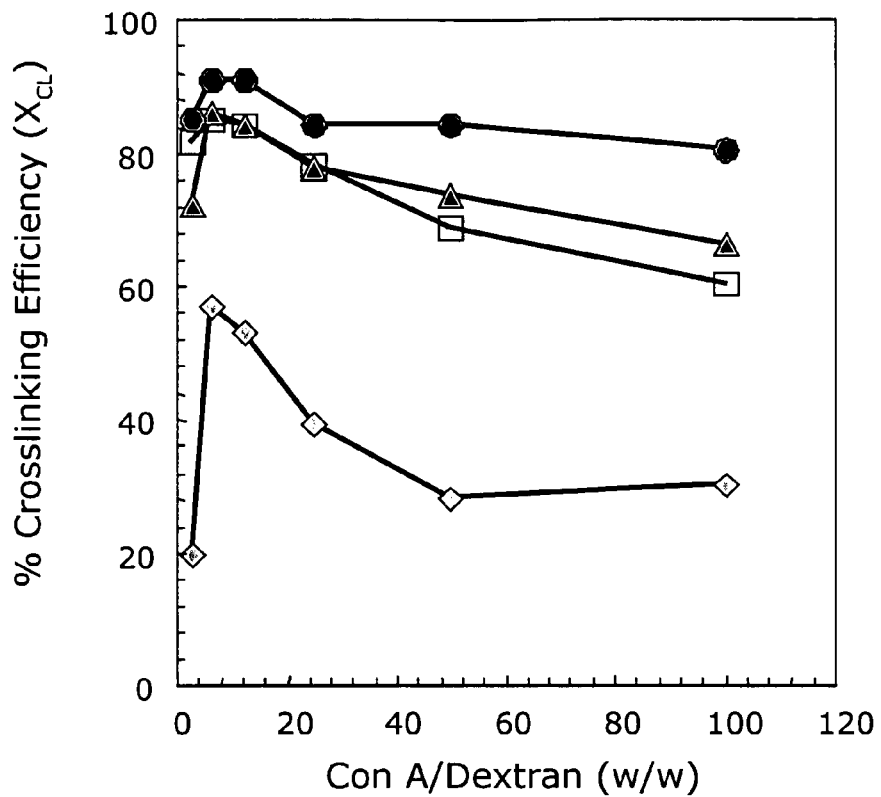
FIG. 4 is a graph of gel cross-linking efficiency vs. Con A/dextran ratio at a constant [Con A]=50 mg/ml (dextran molecular weight: 70 K (diamond), 170K (square), 280K (triangle) and 500K (circle)).

Crosslinking efficiency ($X_{CL}$) was calculated according to Equation 1 and found to vary with both the Con A/dextran ratio and the dextran MW (FIG. 4). For each MW, $X_{CL}$ reaches a maximum at a Con A/dextran ratio of about six. Soluble Con A-dextran complexes rather than insoluble networks form at lower ratios due to an insufficient number of protein binding sites. At higher ratios, precipitates form that are virtually insensitive to sugar concentration. The maximum $X_{CL}$ is only 60% for the dextran with MW=70 K, but increases to 90% for the higher MW dextrans. It appears that lower MW dextrans can form soluble Con A-polymer conjugates that do not gel, thereby decreasing the $X_{CL}$.

Glucose-Sensitive Gel Dissolution

Freeze-dried gels synthesized at a Con A/dextran ratio of 6.1 from dextran of MW=70 K (Dex-70) and dextran of MW=500 K (Dex-500) were placed in 20 mM pH 7 buffered saline solutions containing 50, 100, and 400 mg/dl glucose. Gel dissolution was measured by detecting dextran fluorescence in the supernatant and normalizing the calculated concentrations to those obtained after complete dissolution. The gels dissolve at markedly different rates depending on the glucose concentration in the release medium. The Dex-70 (FIG. 5) and Dex-500 (FIG. 6) exhibit sustained degradation over days at low glucose concentrations, but completely dissolve in about two hours at 400 mg/dl. The Dex-70 gels dissolve faster at the lower glucose concentrations than the Dex-500 gels and are more sensitive to changes between 50 and 100 mg/dl.

Figure 7:
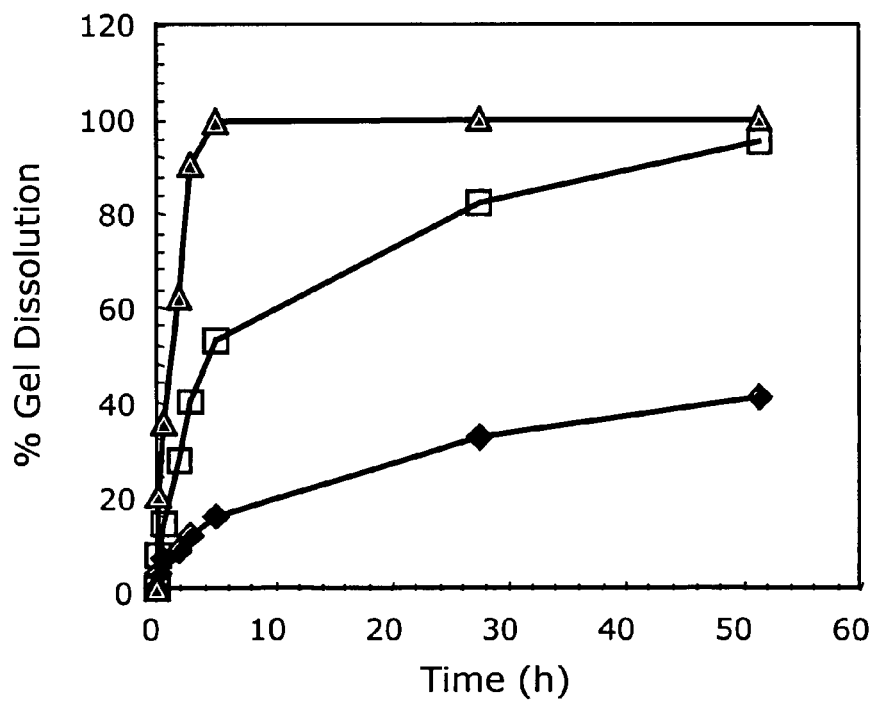
FIG. 7 is a graph illustrating gel dissolution at 37° C. pH 7.0 BES buffered saline solution at [glucose]=50 mg/dl (diamond), 100 mg/dl (square), and 400 mg/dl (triangle) (dextran MW=500K, Con A/dextran=6.1 (w/w)).

Freeze-dried Dex-500 gels were also dissolved in buffered saline solutions at 37° C. to determine the effect of temperature on dissolution rates. As shown in FIG. 7, the Dex-500 gels are more glucose-sensitive and dissolve faster at elevated temperatures. In fact, at 37° C., the gels clearly distinguish between 50 mg/dl (hypoglycemic), 100 mg/dl (normal), and 400 mg/dl (hyperglycemic) glucose concentrations, representing an ideal formulation for practical application. The temperature-dependent effects may be due to an increase in Con A binding affinity for free glucose versus polymeric glucose, leading to gel disruption at lower free sugar concentrations. Another possible explanation is a temperature-dependent increase in polymer diffusion from the gel after competitive binding has taken place.

Figure 5:
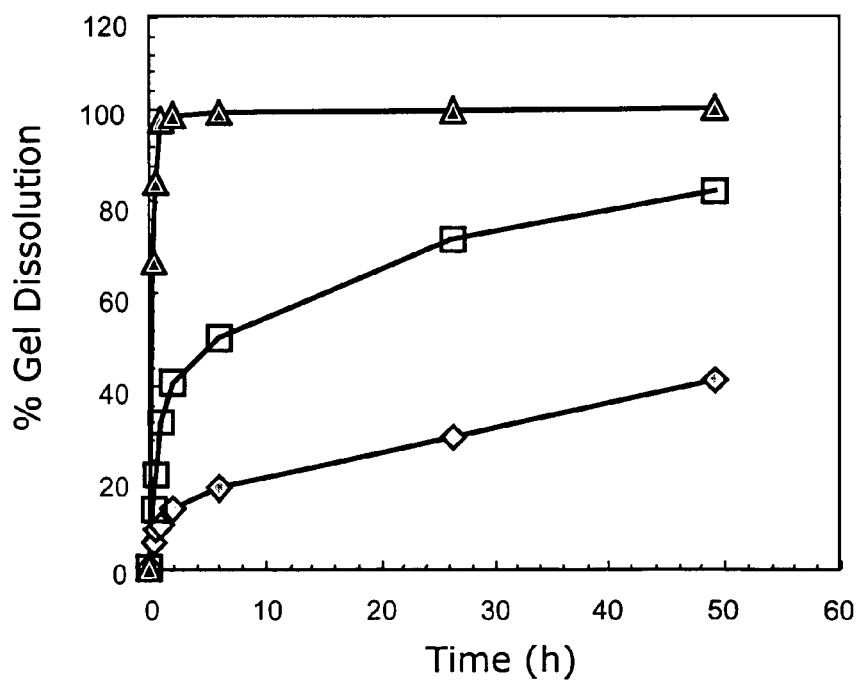
FIG. 5 is a graph showing room-temperature gel dissolution pH 7.0 BES buffered saline solution at [glucose]=50 mg/dl (diamond), 100 mg/dl (square), and 400 mg/dl (triangle) (dextran MW=70K, Con A/dextran=6.1 (w/w)).
Figure 6:
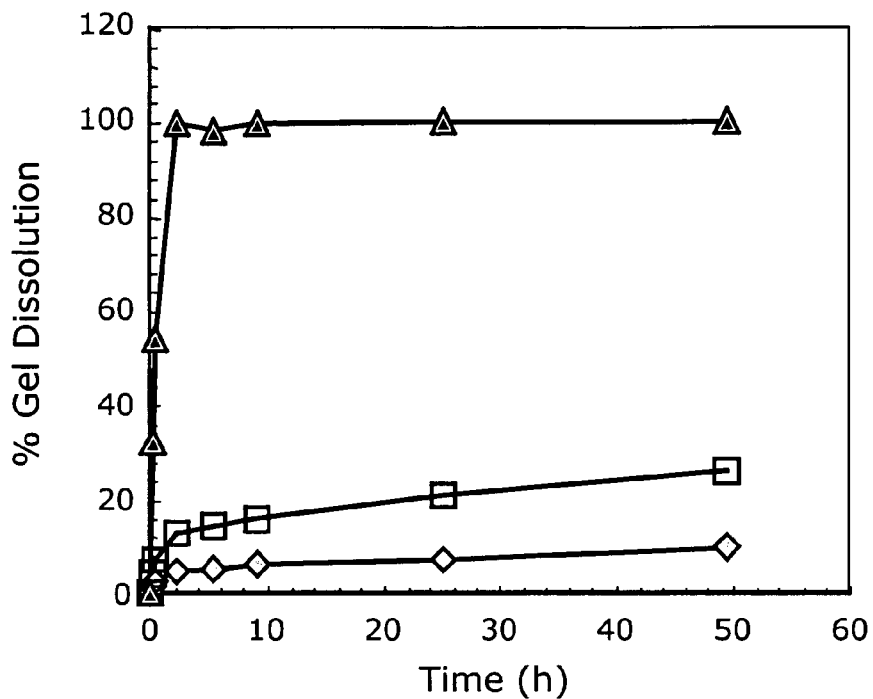
FIG. 6 is a graph showing room-temperature gel dissolution pH 7.0 BES buffered saline solution at [glucose]=50 mg/dl (diamond), 100 mg/dl (square), and 400 mg/dl (triangle) (dextran MW=500K, Con A/dextran=6.1 (w/w)).
Figure 8:
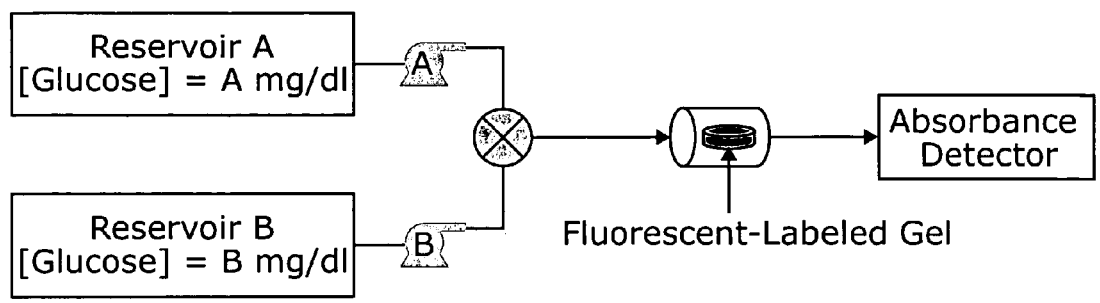
FIG. 8 is a schematic diagram of a flow cell constructed to determine intrinsic glucose sensitivity and perform glucose cycling studies.

FIGS. 5-7 demonstrate glucose-sensitive gel dissolution, but fail to quantify two key points: (1) intrinsic glucose-sensitivity (IGS), the range of glucose concentrations over which there is significant dissolution, and (2) reversibility of response. To determine the IGS for each of the materials, we constructed a flow cell as shown in FIG. 8. The inlet to the flow cell is connected to two reservoirs containing buffered saline solutions with low and high glucose concentrations. The gels were equilibrated at 0 mg/dl for two hours and then the inlet glucose concentration was ramped at a rate of 8.3 mg/dl/min by changing the ratio of flow rates from the two reservoirs. The outlet of the flow cell was connected to an absorbance detector to continuously determine the amount of dextran dissolved at a wavelength equal to the maximum $\lambda_{ex}$ of the dextran fluorophore.

Figure 9:
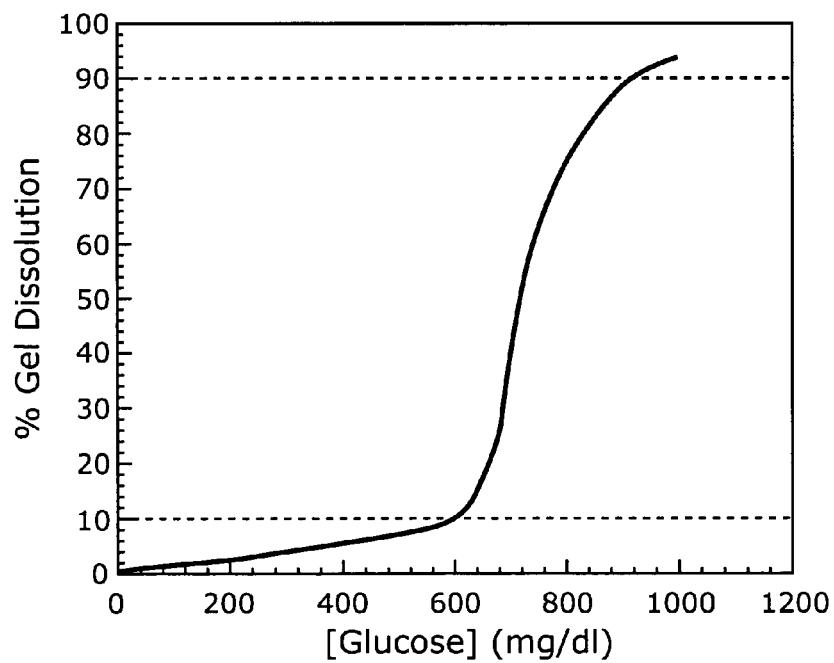
FIG. 9 is a graph describing the room-temperature intrinsic glucose sensitivity (IGS) curve obtained from a flow cell such as the one in FIG. 8 with a glucose ramp rate of 8.3 mg/dl/min and a gel with Con A/dextran=6.10 (w/w).

The amount of dissolved dextran was integrated over time and normalized by that originally contained within the gel (FIG. 9). In addition, samples were taken at regular intervals and diluted appropriately to measure the glucose concentration with a Prestige™ Smart System glucose meter. The glucose concentration was confirmed to vary linearly over time at the predetermined rate of 8.3 mg/dl/min. In this experiment, 10% of the Dex-70 gel dissolved before the glucose concentration reached 600 mg/dl and 90% by 860 mg/dl. Current experiments are aimed at correlating glucose concentration at 10% gel dissolution ($G_{10\%}$) for gels that demonstrate markedly different release profiles in the batch experiments outlined before. The goal was to obtain a single parameter, such as $G_{10\%}$, that captures the IGS for each formulation.

Figure 10:
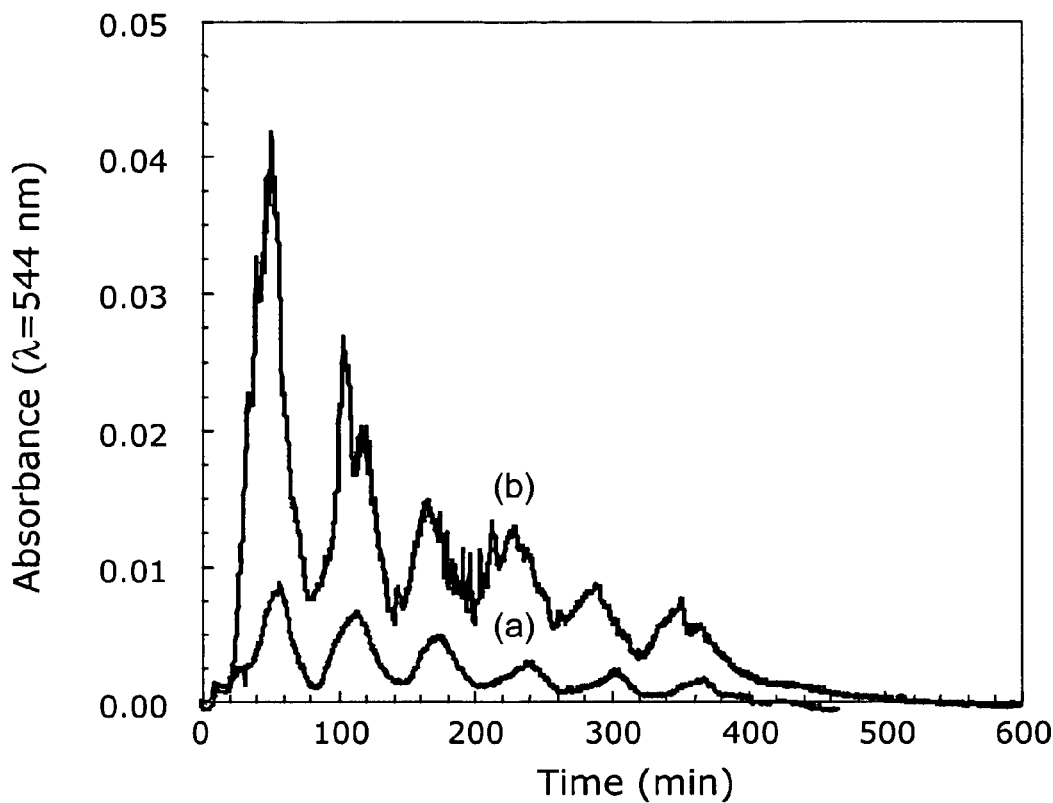
FIG. 10 is a graph illustrating the results of room-temperature glucose cycling studies obtained with the flow cell of FIG. 8 with $[glucose]_A$=50 mg/dl and $[glucose]_B$=(A) 250 mg/dl or (B) 500 mg/dl and Con A/dextran=6.1 (w/w).

To determine the reversibility of response, the flow cell experiment was adapted to cycle the inlet glucose concentration from a low to high value in 30 min and then back down again in another 30 min. Gel dissolution was monitored by continuously measuring the absorbance at $\lambda_{max}$ (544 nm) of the fluorescently labeled dextran. FIG. 10 shows that the gels are capable of releasing at a higher rate as the glucose concentration increases, but, more importantly, can also slow down their release as the glucose concentration decreases. As expected, the extent of the response is governed by the overall glucose concentration range. When the gels are cycled between 50 and 500 mg/dl, the extent of the response diminishes more rapidly after each cycle as the gel approaches complete dissolution. The flow cell, therefore, represents a powerful tool for characterizing both the glucose sensitivity and dynamic response of our materials.

EXAMPLE 2

Modifying Glucose Sensitivity of Hydrogels

Although the Con A-dextran gels appear to respond remarkably well to glucose concentrations in the physiological range, it may be beneficial to modify the gel IGS for certain practical situations. Depending on the site of application (e.g. subcutaneous tissue, intravenous circulation, specific organs, etc.), the local sugar concentration may vary a great deal for a given physiological state, such as fasting or post-prandial. For example, changes in glucose concentration in the subcutaneous fluid (SCF) are well correlated to changes in intravenous (IV) concentration, but the average value in the SCF may be much lower (S. J. Updike, M. C. Shults, B. J. Gilligan, R. K. Rhodes, Diabetes Care 23, 208 (2000)). In addition, one may desire more than one type of glucose-regulated response. One material may be designed with an IGS for normoglycemic concentrations to provide well-regulated long-term insulin release. Another material may be designed with a much higher IGS to release insulin only after meal-time blood sugar rises. Because the dextran-Con A materials exhibit significant degradation at normoglycemic concentrations, we developed methods to increase the IGS through covalent glycosylation of the dextran polymer.

Mannose is known to bind Con A with 3.8 times the affinity as glucose (J. N. Sanders, S. A. Chenoweth, F. P. Schwarz, J. Inorg. Biochem. 70, 71 (1998)). Therefore, it is expected that covalent modification of dextran with mannose will result in a gel that only responds to much higher sugar concentrations. Dextran was modified with mannose to produce mannosylated dextran (ManDex) using the divinylsulfone (DVS) procedure described in R. Ballerstadt, J. S. Schultz, Anal. Chim. Acta 345, 203 (1997), the contents of which are incorporated herein by reference. Briefly, FITC-Dex is added to a pH 11.4 bicarbonate buffer and activated with DVS. D-mannose is then added and allowed to react for ~1 hour at room temperature, after which glycine is added to neutralize and quench the reaction. The resulting polymer is dialyzed exhaustively against deionized water and finally lyophilized.

Figure 11A:
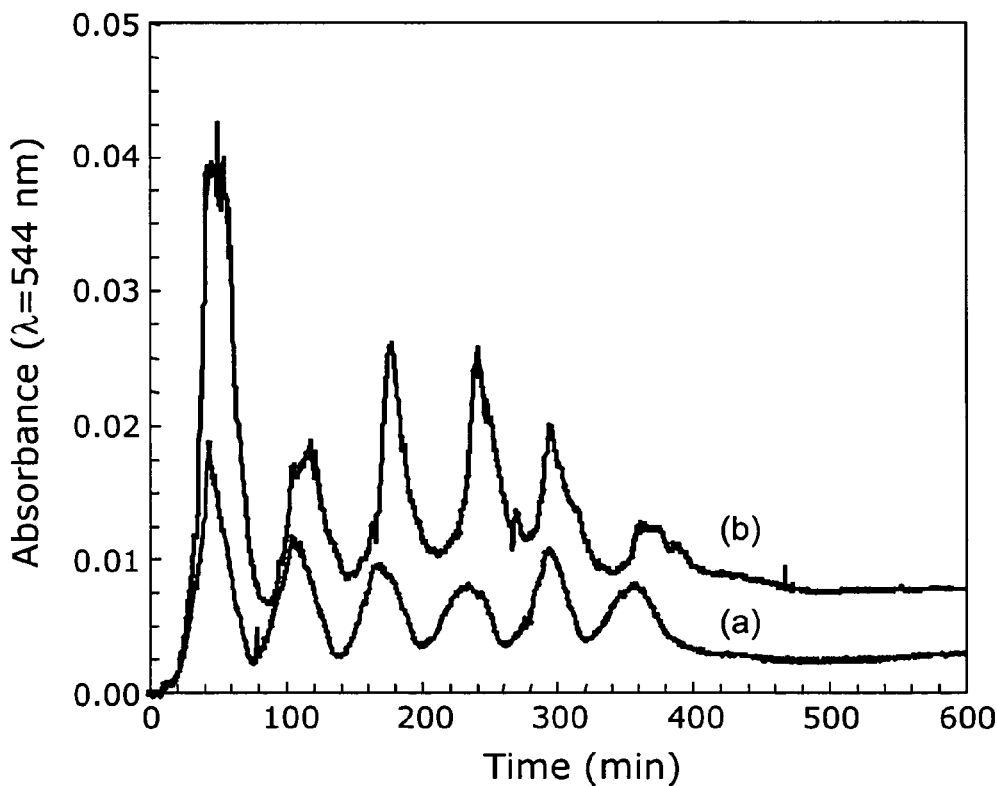
FIG. 11A illustrates room-temperature glucose cycling studies obtained with the flow cell of FIG. 8 and a gel of cross-linked mannosylated dextran.
Figure 11B:
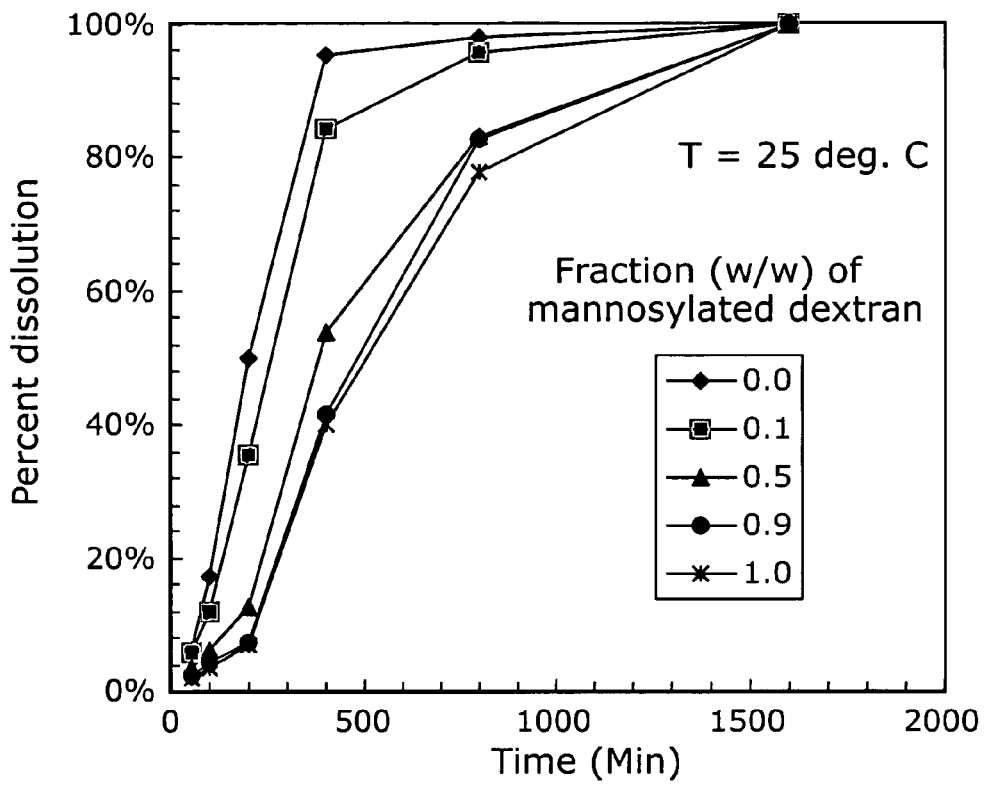
FIGS. 11B-C are graphs illustrating the variation in the stepwise dissolution of ConA/Dextran gels containing various amounts of ManDex at (B) room temperature and (C) 37° C. ([ConA]=50 mg/ml, ConA/Dextran=3:1 (w/w), fraction of ManDex=0 (diamond), 0.1 (square), 0.5 (triangle), 0.9 (circle), 1.0 (asterisk)).
Figure 11C:
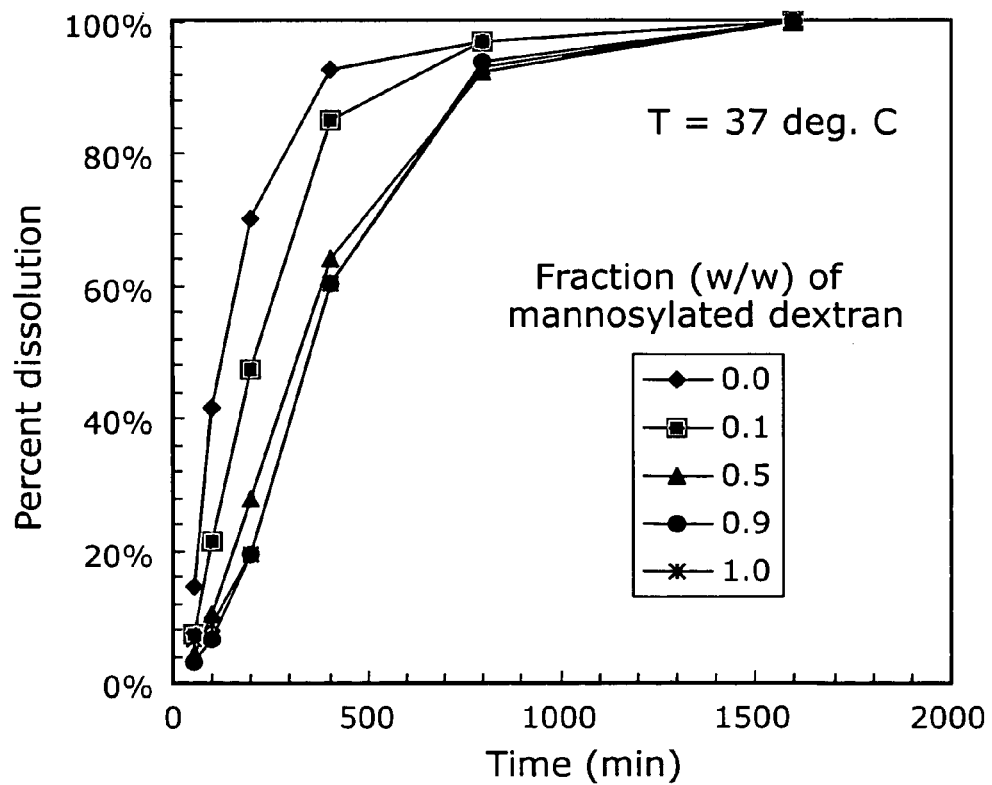

Gels constructed from ManDex-70 at a Con A/ManDex ratio of 6:1 were placed in the flow cell and the inlet glucose concentration was cycled between 50 and 250 mg/dl (a) and 50 and 500 mg/dl (b), as was done for the unmodified Dex-70 gels. FIG. 11A shows that the gel response is even more reversible than the unmodified case, especially for the 50-500 mg/dl cycle. A majority of the gel was still intact after the six cycles, indicating increased IGS for the ManDex formulation. FIGS. 11B and 11C show that mannosylation significantly slows dissolution.

EXAMPLE 3

Insulin Encapsulation and Release

The dextran gels were originally designed to have a pore structure that inhibits insulin diffusion at low sugar concentrations, but releases insulin as the gel dissolves at higher concentrations. To load the gels with insulin, the synthesis media was modified to contain a solution of bovine insulin at 1 mg/ml. After synthesis and washing, the Dex-70 gels (Con A/dextran=6.1 (w/w)) contained approximately 1% bovine insulin on a dry weight basis as determined by HPLC using a C18 column (Waters Symmetry 5 mm C18, 250×4.6 mm) and a mobile phase of 1.4 ml/min containing 37% v/v acetonitrile in a pH 2.4 sodium sulphate/phosphoric acid buffer. The insulin-loaded gels were then placed in pH 7 buffered saline containing glucose concentrations of 50, 100, and 400 mg/dl, and samples were taken at regular time intervals to measure both dextran and insulin release by HPLC.

Figure 12A:
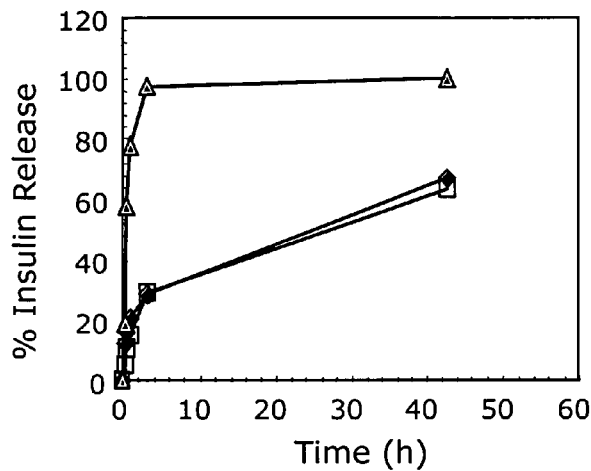
FIG. 12 includes graphs of (A) insulin release and (B) room-temperature gel dissolution in pH 7.0 BES buffered saline solution at [glucose]=50 mg/dl (diamond), 100 mg/dl (square), and 400 mg/dl (triangle).
FIG. 12C is a graph depicting the room temperature insulin release over time from methacrylated dextran nanoparticles (0.99 mol methacrylate/mol dextran subunit, MW=40K) at glucose concentrations of 100 mg/dl (diamond), 1000 mg/ml (square), and 10,000 mg/ml (triangle).
Figure 12B:
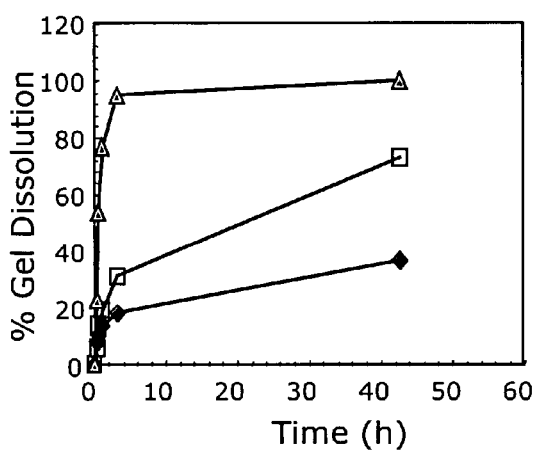
Figure 13A:
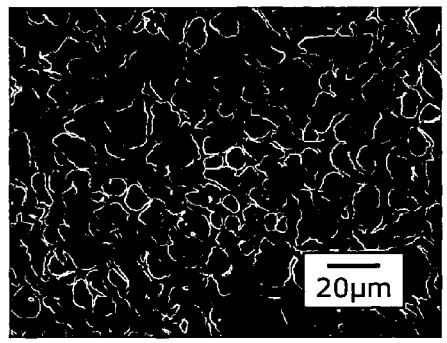
FIGS. 13A-B are environmental scanning electron micrographs of freeze-dried gel (Con A/dextran=6.1 (w/w), dextran MW=70K).
Figure 13B:
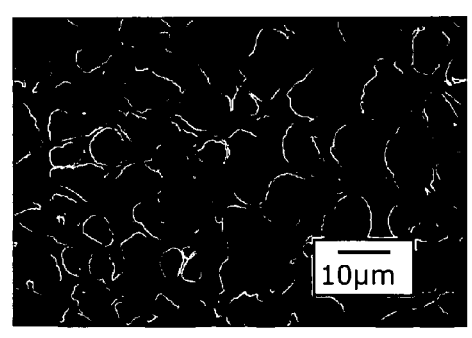

FIG. 12A shows that insulin release profiles are indistinguishable between 50 and 100 mg/dl, but much more rapid at the higher 400 mg/dl glucose concentration. At the low sugar concentrations, gel dissolution is fairly slow, as shown in FIG. 12B, but the pore size and porosity are quite high, as shown in the ESEM micrographs (FIG. 13). Insulin release is therefore governed by hindered diffusion through the porous gel at low sugar concentrations. At 400 mg/dl, the gel completely dissolves, thereby releasing the entire insulin content.

Figure 12C:
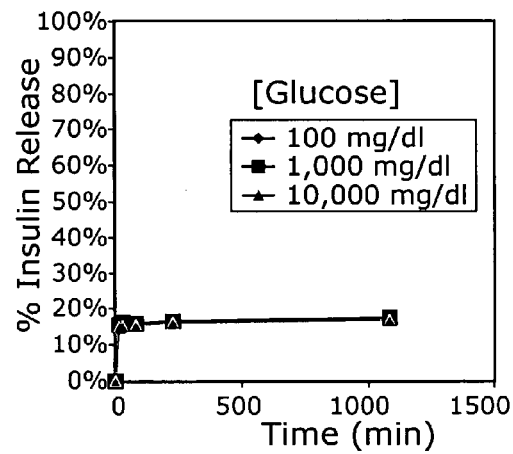

We have employed two methods to improve control over insulin release rates at low sugar concentrations. One way is to modify the gel pore size to approach that of the insulin molecule and then increase the pore size considerably in response to small increases in glucose concentration. To accomplish this, the dextran was modified with polymerizable methacrylate groups according to the procedure described previously to provide sites for chemical crosslinking (S. H. Kim, C. C. Chu, *J. Biomed. Mater. Res.* 49, 517 (1999)). The chemically crosslinked gels indeed allow minimal insulin release at low sugar concentrations, but fail to respond at elevated sugar concentrations (FIG. 12C). In these cases, the glucose-insensitive chemical crosslinking dominates the pore structure and the resulting insulin release profiles.

The second method, which has shown considerable promise, is to closely associate insulin to the dissolving dextran. By doing so, the insulin release would exactly match the gel dissolution profiles. Significant research has been carried out over the years to graft proteins and drugs, including insulin, to dextran in an effort to modify their circulation time and absorption profiles. The most common conjugation method involves activating dextran with cyanogen bromide (CNBr) at pH 10 in water, followed by reaction with insulin (L. Kagedal, S. Akerstrom, *Acta. Chem. Scand.* 25, 1855 (1971)). Using this method, insulin has been conjugated to dextran of MW's between 10 and 2,000 kDa with degrees of substitution (DS) ranging between 1% and 30%. The reported bioactivity of the conjugates varies between 10% and 100% of unmodified insulin, but in all cases a glucose lowering effect was observed in vivo (L. Kagedal, et all, *Acta. Chem. Scand.* 25, 1855 (1971); K. J. Armstrong, M. W. Noall, J. E. Stouffer, *Biochem. Biophys. Res. Commun.* 47, 354 (1972); Y. Sakamoto, Y. Akanuma, K. Kosaka, B. Jeanrenaud, *Biochim. Biophys. Acta* 498, 102 (1977); F. Suzuki, Y. Daikuhara, N. Ono, Y. Takeda, *Endocrinology* 90, 1220 (1972)).

The degree of insulin substitution was determined by UV spectroscopy at 280 nm and confirmed by the Bradford protein assay to be 36±4% (w/w). Gels were formed from Con A and dextran-insulin according to the procedure described before. The insulin encapsulation efficiency was found to increase by over an order of magnitude and the insulin loading increased by almost 8× through insulin conjugation. Con A-dextran-insulin gels with a Con A/dextran-insulin ratio of 4 were placed in pH 7 buffered saline solutions containing 50, 100, and 400 mg/dl of glucose, and samples were taken at regular time intervals to measure the dextran-insulin release. The dextran-insulin concentration was determined by HPLC using a SuperDex G75 column (Amersham Biosciences) and a pH 7 BES buffered saline mobile phase of 1.0 mmin. The Superdex column separates any Con A released, so that the dextran-insulin may be uniquely determined at $\lambda$=280 nm.

Figure 14:
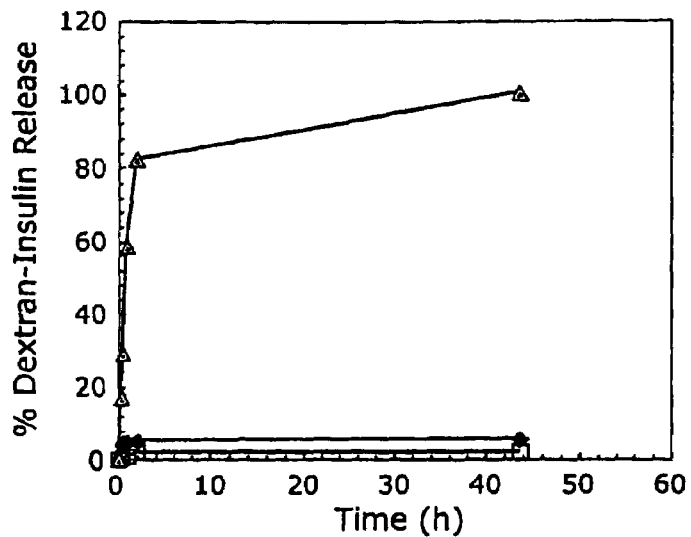
FIG. 14 is a graph illustrating room-temperature dextran-insulin release at [glucose]=50 mg/dl. (diamond), 100 mg/dl (square), and 400 mg/dl (triangle).

The dextran-insulin release profiles of Dex-70 gels with Con A/dextran-insulin=4 (w/w) shown in FIG. 14 demonstrate remarkably low insulin leakage at the lower sugar concentrations and rapid release at the hyperglycemic glucose concentration of 400 mg/dl.

EXAMPLE 4

In Vivo Evaluation

Con A was dissolved in pH 7 BES buffer containing 1 M NaCl and 1 mM $Mn^{2+}$ and $Ca^{2+}$ at a concentration of 100 mg/ml and sterile filtered through a 0.45 micron syringe-driven membrane filter. Dextran (70 K) functionalized with 15% human insulin (w/w) was dissolved in pH 7 BES buffer containing 0.15 M NaCl at a concentration of 20 mg/ml and sterile filtered through a 0.45 micron syringe-driven membrane filter. Gels were synthesized in a sterile laminar flow hood using standard aseptic procedures by combining 0.20 ml of Con A solution with 0.20 ml of dextran-insulin solution (single dose), 0.40 ml of Con A solution with 0.40 ml of dextran-insulin solution (double dose), or 0.60 ml of Con A solution with 0.60 ml of dextran-insulin solution (triple dose). The resulting gels were isolated and washed exhaustively with sterile phosphate buffered saline solution and stored overnight prior to transplantation.

Figure 32:
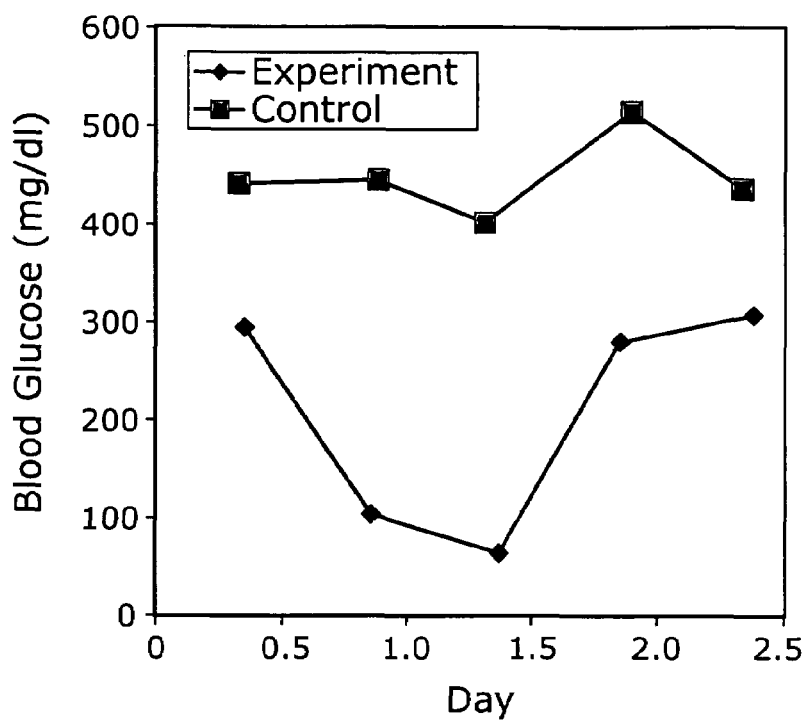
FIG. 32 is a graph illustrating the variation of blood glucose with time in STZ-induced diabetic Sprague-Dawley rats given a dose of gel constructed from ConA (50 mg/ml) and dextran-insulin MW 70K (20 g/ml) (diamond) or saline solution (square).
Figure 33:
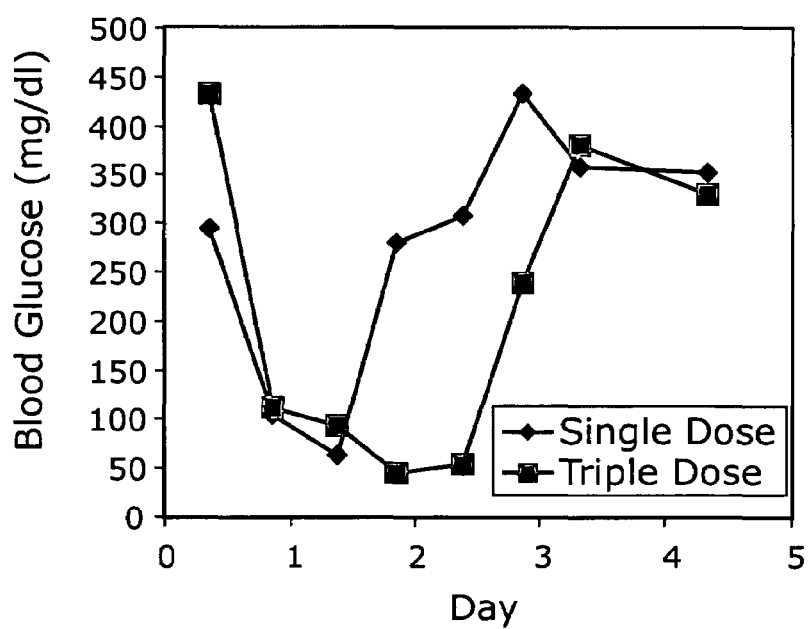
FIG. 33 is a graph illustrating the variation of blood glucose with time in STZ-induced diabetic Sprague-Dawley rats given a single dose (diamond) or a triple dose (square) of gel constructed from ConA (50 mg/ml) and dextran-insulin MW 70K (20 g/ml).

Male Sprague-Dawley rats (Charles River Laboratories) weighing approximately 250 g were injected with 80 mg/kg of streptozotocin to induce diabetes. After one week, rats with blood glucose levels greater than 300 mg/dl were used in the following experiments. Gels (experiment) or saline (control) solution were placed in the intraperitoneal cavity through an incision in the abdominal skin and muscular layers. Blood samples were taken from the tail vein over time and measured for glucose concentration using a MediSense glucometer. FIG. 32 demonstrates the ability of a single dose to control diabetic glucose levels over a one and a half day period. Furthermore, FIG. 33 shows that glucose control is extended to three days by just tripling the dose of glucose-sensitive gel.

Figure 34:
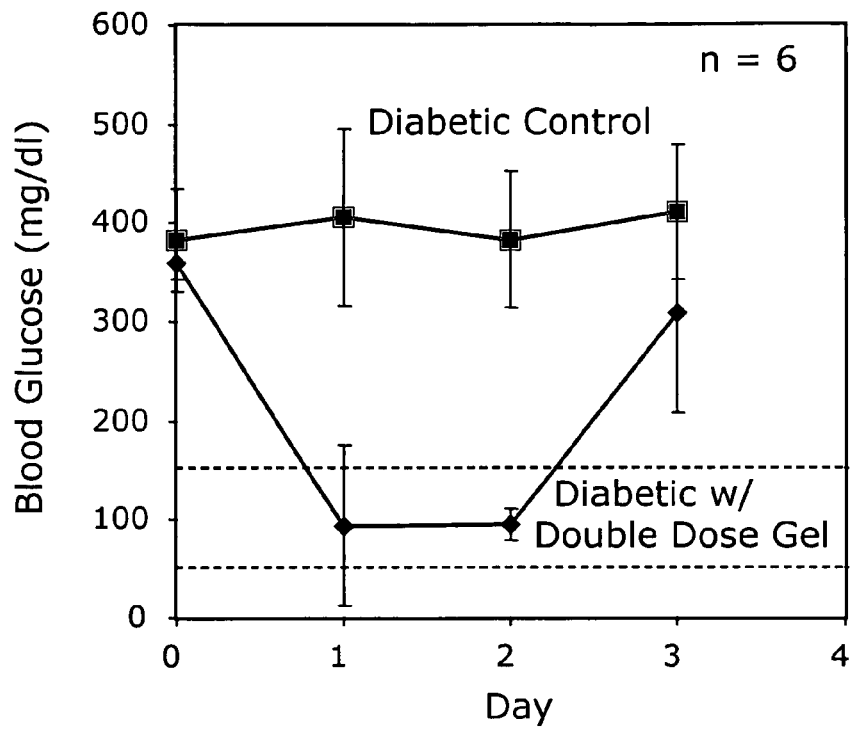
FIG. 34 is a graph illustrating the variation of blood glucose with time in STZ-induced diabetic Sprague-Dawley rats given a dose of double dose of gel constructed from ConA (50 mg/ml) and dextran-insulin MW 70K (20 g/ml) (diamond) or saline solution (square) after fasting for 6 hours.
Figure 35:
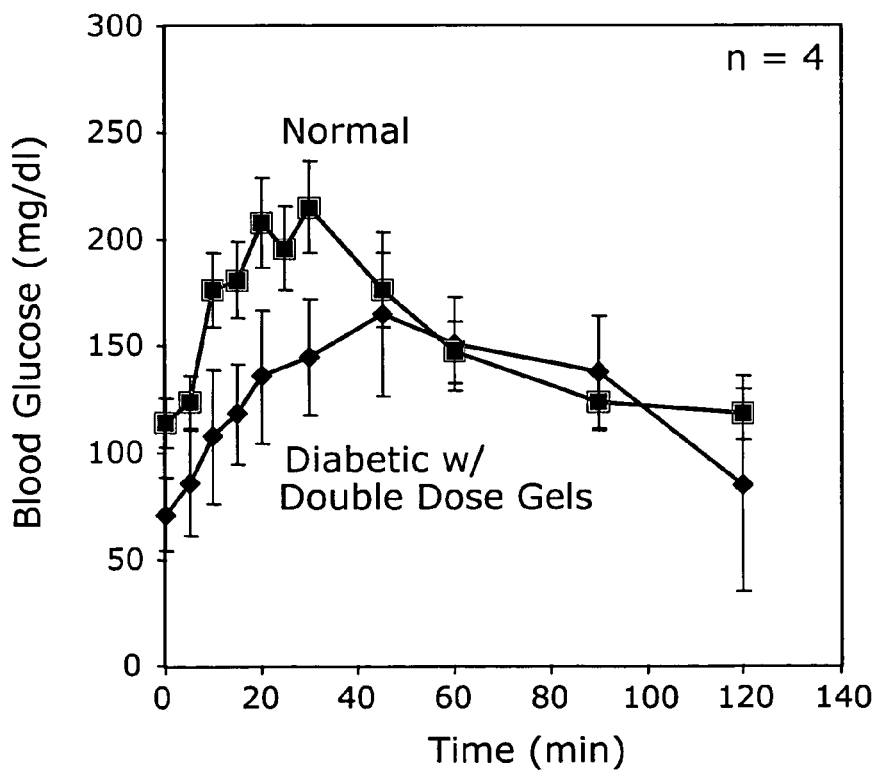
FIG. 35 is a graph illustrating the variation of blood glucose with time in STZ-induced diabetic Sprague-Dawley rats given a dose of double dose of gel constructed from ConA (50 mg/ml) and dextran-insulin MW 70K (20 g/ml) (diamond) or saline solution (square) during a glucose tolerance test.

In another experiment double dose gels (experiment) or saline (control) solution were placed in the intraperitoneal cavity through an incision in the abdominal skin and muscular layers. The rats were fasted in the morning for six hours, and blood samples were taken from the tail vein after fasting and measured for glucose concentration using a MediSense glucometer. FIG. 34 demonstrates the ability of a double dose gel to control diabetic fasting glucose levels over a two and a half day period. In select animals, an intraperitoneal glucose tolerance test (IPGTT) was performed after the six hour fast. The IPGTT was performed by injecting a 45% glucose solution intraperitoneally at a dose of 1 g/kg of body weight. Blood samples were taken at frequent intervals over the course of two hours. FIG. 35 shows the ability of double dose gels to minimize the extent and timing of the spike in blood glucose levels. The glucose tolerance compares favorably to that obtained from normal-non diabetic rats subjected to the same procedure.

EXAMPLE 5

Reverse Microemulsion Formulation

The existence of RM's was identified by preparing various pseudoternary compositions and evaluating the optical clarity of the mixture. Clear, transparent formulations are indicative of stable RM's as the size of the aqueous domains are much smaller than the wavelength of light (M. J. Lawrence, G. D. Rees, *Adv. Drug Deliv. Rev.* 45, 89 (2000)). To quantify the optical clarity of a particular system at a number of compositions while minimizing the experimental time and materials required, a rapid screening approach was developed. Briefly, varying amounts of surfactant (3:2 w/w Tween 80/Span 80) and oil (3:1 w/w Captex 355/Capmul MCM) were micropipetted into a glass, flat-bottomed, 96-well microplate (500 µl well capacity, Alltech) and mixed thoroughly. The appropriate amount of aqueous solution was then added to make a total volume of 350 µl, and mixed in such a way that each well contained a specific ternary composition. Each composition was run in duplicate, and absorbance values for all 96 wells were collected at a wavelength of 450 nm using a VERSAmax microplate reader (Molecular Devices, Sunnyvale, Calif.) to quantify turbidity.

The data resulting from such experiments were plotted on a pseudoternary contour diagram, thereby yielding a pseudoternary surface. FIG. 15A depicts the pseudoternary surface obtained from our rapid screening approach, which agrees remarkably well with the one in the literature obtained by multiple cloud point titrations (S. Watnasirichaikul, N. M. Davies, T. Rades, I. G. Tucker, *Pharm. Res.* 17, 684 (2000)). DLS results (FIGS. 15B-D) obtained at select ternary compositions confirm reverse microemulsion (RM) existence throughout the region of optical transparency. As the aqueous concentration, $\phi_A$, increases at a constant concentration of surfactant, $\phi_S$, (FIG. 15B) and at a constant concentration of oil, $\phi_O$ (FIG. 15C), the dispersed phase progresses from reverse micelles to larger water-swollen reverse micelles until finally a turbid multi-phase region is obtained. As $\phi_S$ increases at a constant $\phi_A$ (FIG. 15D), the system transitions from a kinetically stabilized reverse emulsion toward a RM containing droplets of decreasing diameter.

Figure 16:
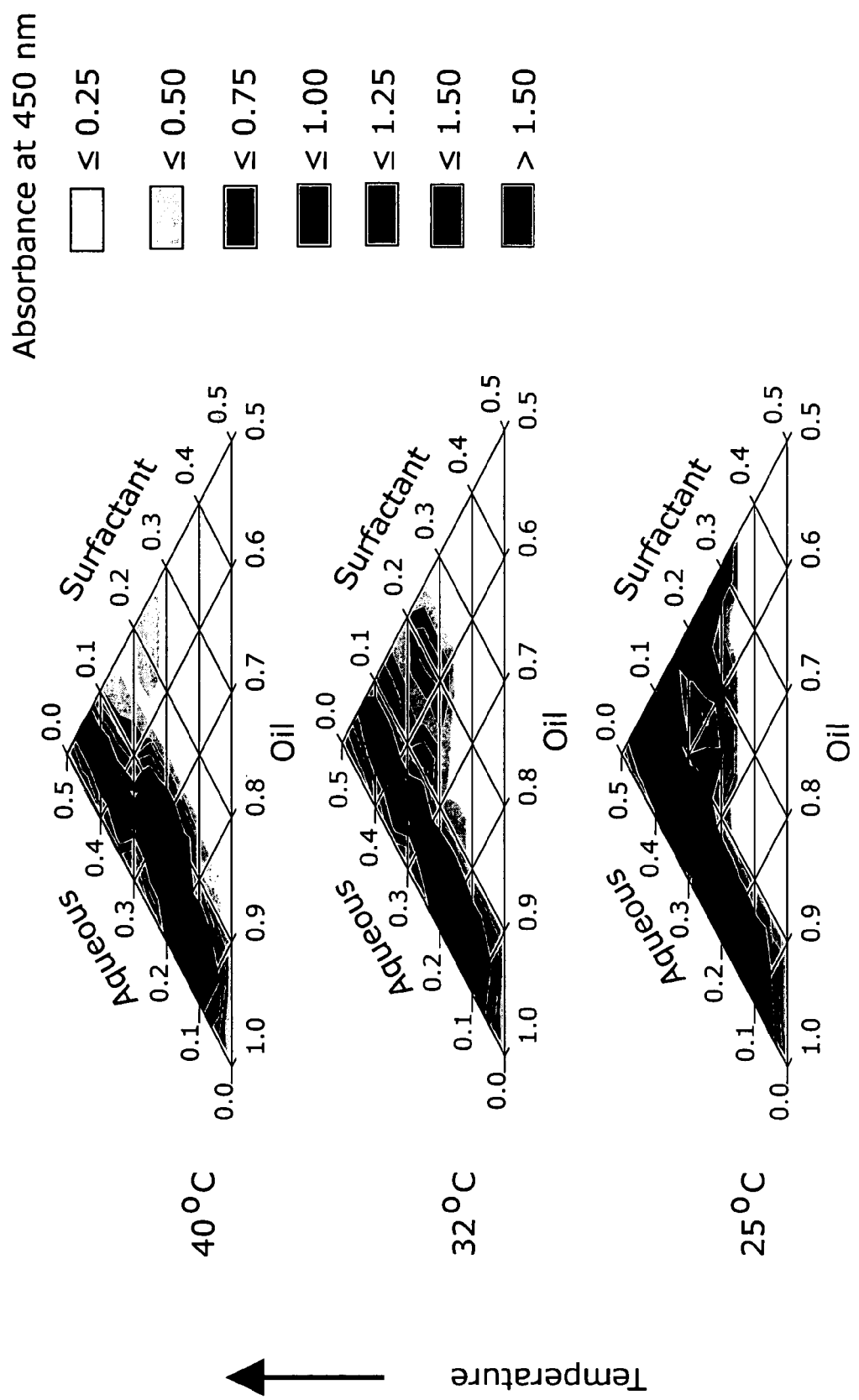
FIG. 16 is a series of ternary phase diagrams illustrating the effect of temperature on reverse microemulsion formation for the mixture described in FIG. 15.

Temperature also influence the formation of RMs containing Con A or insulin. As the temperature increases, less surfactant is required to maintain the desired dispersed phase (FIG. 16). In addition, FIG. 16 demonstrates that, generally, RMs formed at room temperature will not coalesce at higher temperatures, for example, after administration to a patient. The increase in the region of optical clarity also indicates that an increase in temperature during fabrication can increase the yield of particles from a given microemulsion.

EXAMPLE 6

RM Stability in the Presence of Con A, Insulin, or Dextran

Figure 17:
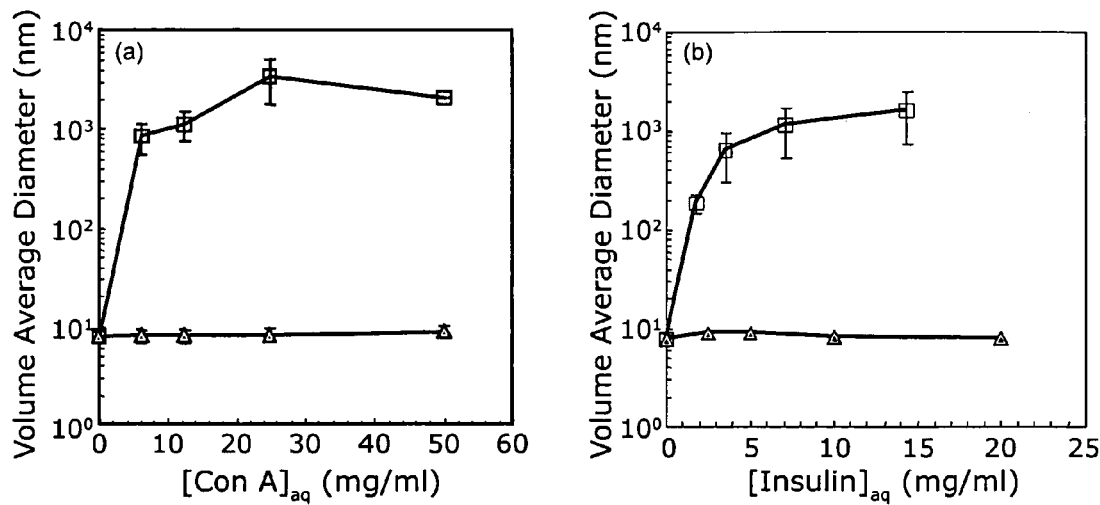
FIG. 17 illustrates dynamic light scattering (DLS) measurements on reverse micoremulsions containing various aqueous concentrations of (A) Con A (B) insulin (aqueous phase: (square) pH 7.0 BES buffered ceiling and (triangle) 0.1 N HCl).

Our early research found that the addition of either Con A or insulin transformed an otherwise optically transparent and stable RM into a turbid, coarse emulsion. FIG. 17 shows the resulting increase in droplet sizes as a function of concentration of both Con A and insulin when dissolved in a pH 7 buffered saline aqueous phase using an RM composition of $\phi_A$=0.10, $\phi_S$=0.25, $\phi_O$=0.65. However, when the proteins were dissolved in a 0.1 N HCl solution, the resulting RM was optically transparent and the size of the dispersed domains approached that of the control.

Possible explanations include pH-dependent differences in protein charge, state of aggregation, and tertiary structure. For example, both Con A and insulin form tetramers and hexamers respectively at neutral pH, which may result in decreased solubility in the RM aqueous domains and increased droplet aggregation. In addition, other researchers have observed large structural changes when proteins were added to reverse micelles as was the case, for instance, with cytochrome c, which enhanced percolation due to increase of attractive interactions between reverse micelles (C. A. T. Laia, W. Brown, M. Almgren, S. M. B. Costa, *Langmuir* 16, 465 (2000)). In our system, these attractive interactions are minimized at low pH, but increase upon neutralization.

To evaluate the effect of dissolved proteins and polymers on RM phase behavior, varying concentrations of each component were dissolved in a 0.1 N HCl aqueous phase before addition to the surfactant/oil mixture. Insulin has minimal effect on the RM existence region as compared to the control (FIG. 18), while Con A gives rise to two distinct regions of optical clarity separated by a turbid region at high surfactant, moderate oil concentrations (FIG. 19).

Figure 20:
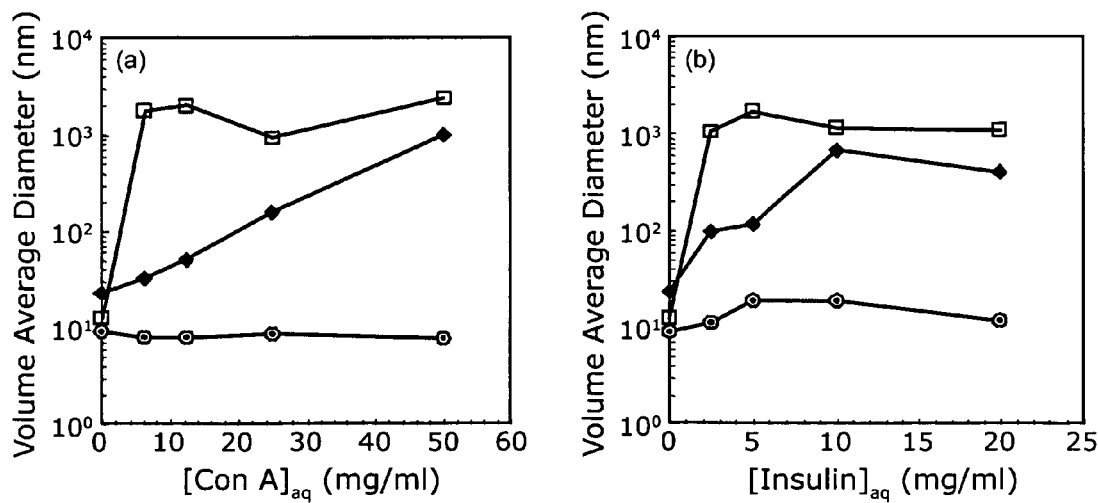
FIG. 20 is a set of graphs illustrating the effect of (A) Con A and (B) insulin concentrations in the aqueous phase on the RM droplet size for (square) Captex 355, (diamond) Myvacet, and (circle) soybean oil systems.
Figure 21A:
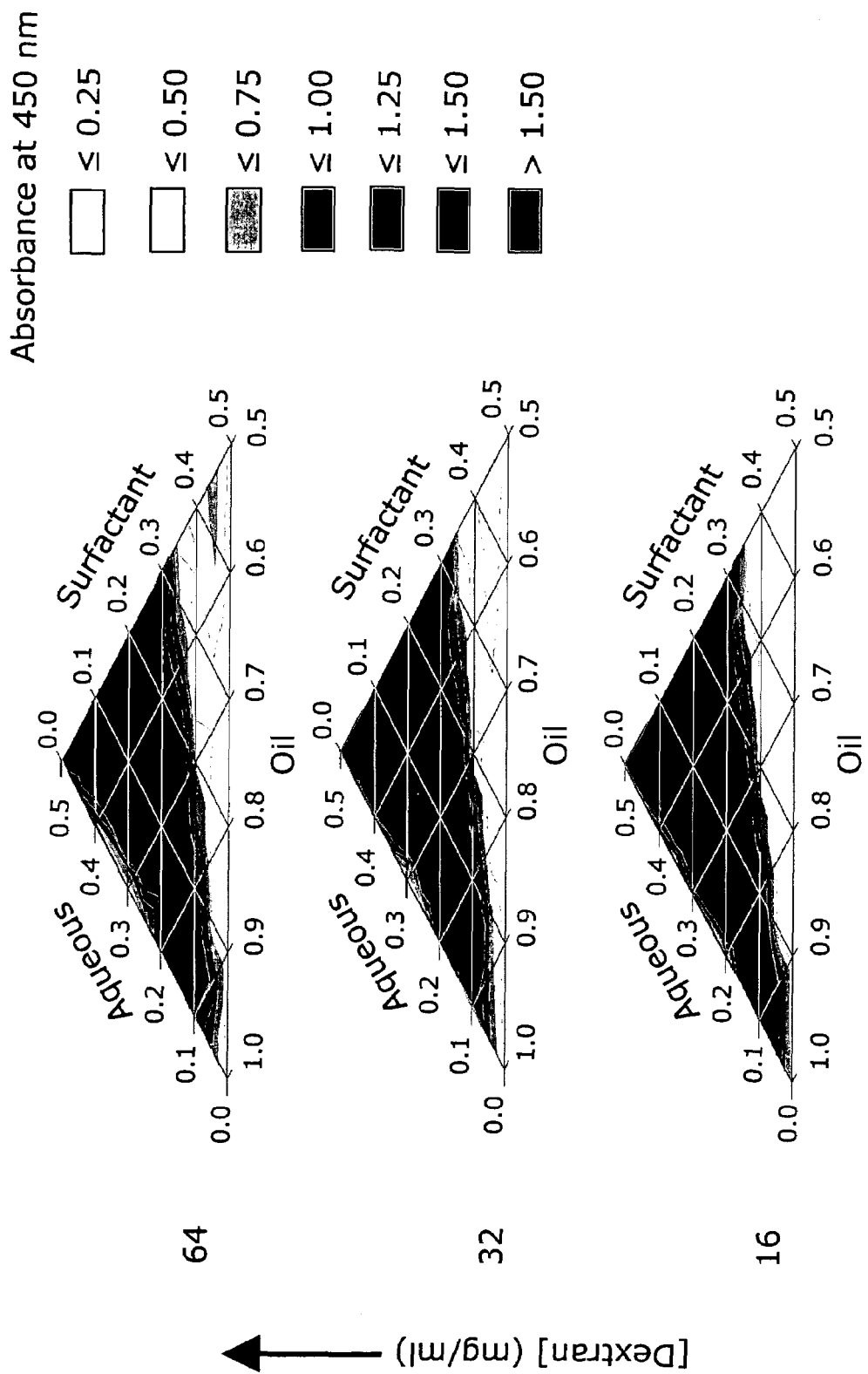
FIGS. 21A-B are sets of ternary phase diagrams illustrating the effect of increasing concentrations of dissolved dextrans on reverse microemulsion formation for molecular weights of (A) 10K and (B) 70K.
Figure 21B:
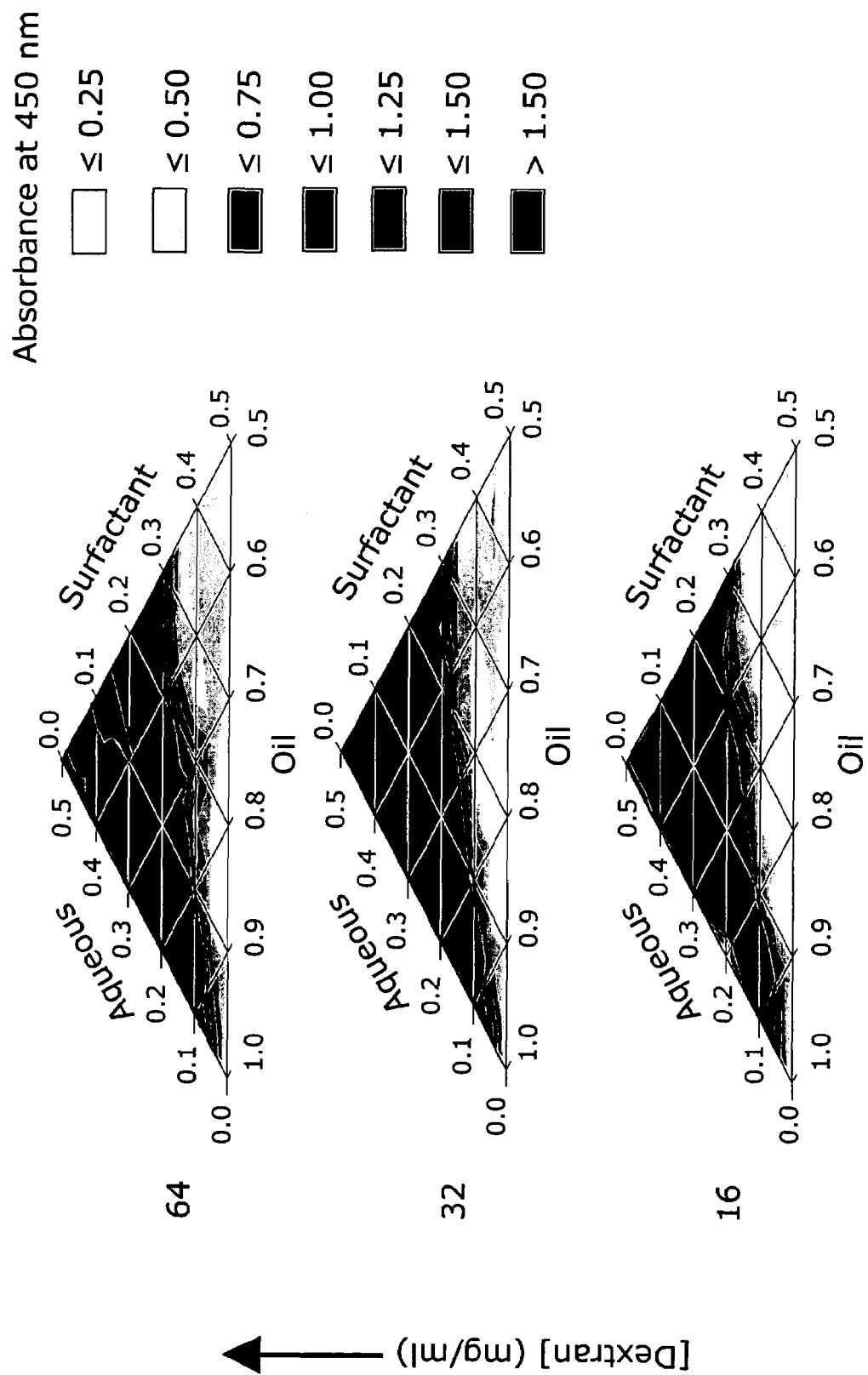
Figure 21C:
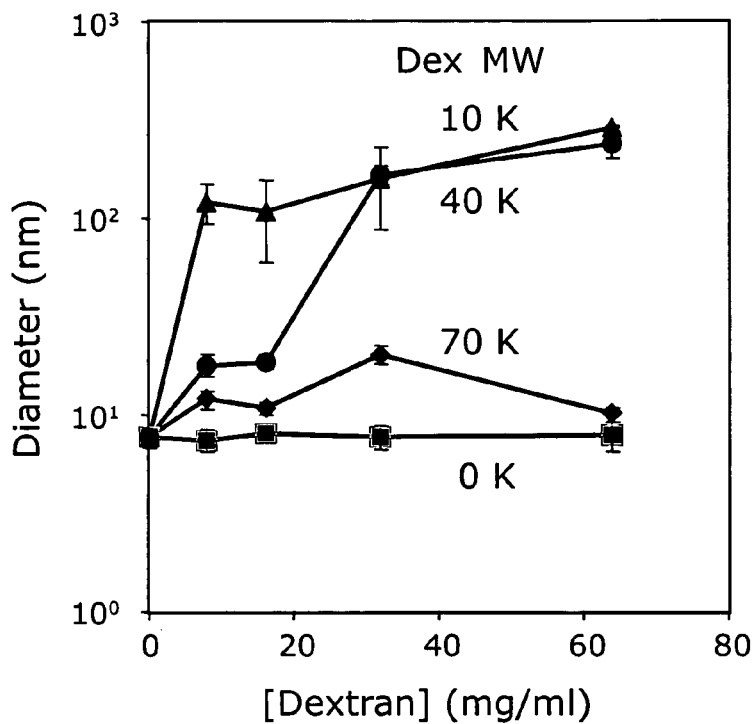
FIG. 21C is a graph illustrating the variation of reverse microemulsion droplet diameter with dextran concentration for varying molecular weights of dextran.
Figure 21D:
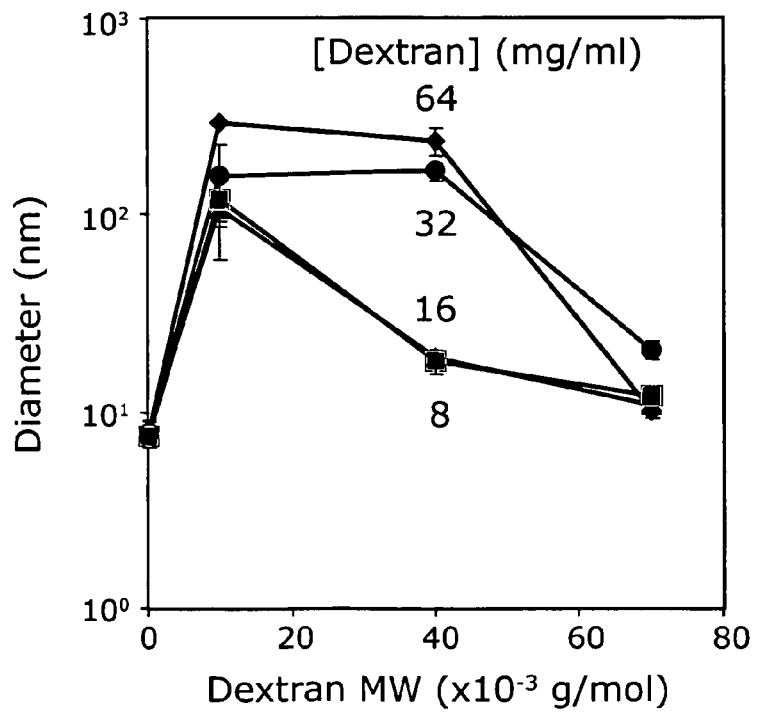
FIG. 21D is a graph illustrating the variation of reverse microemulsion diameter with dextran molecular weight for varying concentrations of dextran.

To determine the extent to which the RM formulation contributes to the protein-induced instability at neutral pH, two other biocompatible RM systems were investigated. One system, Myvacet, is constructed from a Myvacet/Capmul MCM/Myverol 18-92 oil and Cremophor EL surfactant phase. The other system, Soybean, is constructed from a Soybean Oil/Arlacel 186 oil and Tween 80 surfactant phase. FIG. 20 illustrates the droplet size for each system as a function of protein concentration using a pH 7 BES buffered saline aqueous phase and $\phi_A$=0.03, $\phi_S$=0.10, and $\phi_O$=0.87. The results indicate that the Soybean system is minimally affected by the presence of insulin and Con A, while the droplet sizes for the Myvacet system are between those of the Captex and Soybean systems.

FIG. 21 illustrates the effect of dissolved dextran on RM formation. RMs were formed by dissolving dextran in a 0.1 N HCl aqueous phase and adding it to a mixture of surfactant (3:20 w/w Tween 80/Span 80) and oil (3:1 w/w Captex 355/Capmul MCM) at 25° C. For dextran having MW=10, lower concentrations of dextran result in a uniform region of optical clarity, while increasing concentrations result in development of a turbid region at high surfactant concentrations (FIG. 21A) increasing the molecular weight magnifies this effect. FIG. 21B illustrates that the relationship between RM diameter and [dextran] varies with molecular weight but indicates that, regardless of concentration, a molecular weight of 10 results in RMs having a diameter of at least 100 nm.

EXAMPLE 7

Nanoparticle Synthesis, Recovery, and Characterization

Glucose-sensitive nanoparticles were prepared using a RM formulation comprising 65% v/v oil (3:1 w/w Captex 355/Capmul MCM), 25% v/v surfactant (3:2 w/w Tween 80/Span 80), and 10% v/v aqueous phase. To 1.8 ml of a premixed solution of oil and surfactant, 160 µl of a 0.1 N HCl solution containing Con A and dextran of predetermined concentrations were added and mixed thoroughly. Next, 20 µl of a pH 7.0 200 mM BES buffered saline solution containing 1 M NaCl and 20 mM $MnCl_2$ and $CaCl_2$ and 20 µl of a 1 N NaOH solution were added in succession to neutralize the pH and activate Con A/dextran crosslinking. The particle-containing RMs were diluted 1:10 (v/v) with ethanol and centrifuged for 30 min to separate the particles from the ethanol, oil and surfactant. The centrifuge cake was redispersed by sonication and washed twice in ethanol to remove residual oil and surfactants, followed by washing with 20 mM pH 7.0 BES buffered saline solution to remove any unbound dextran. The remaining material was redispersed in ethanol by sonication and dried under vacuum at room temperature for environmental scanning electron microscopy (ESEM) studies (FEI/Philips XL30 FEG ESEM).

Figure 22:
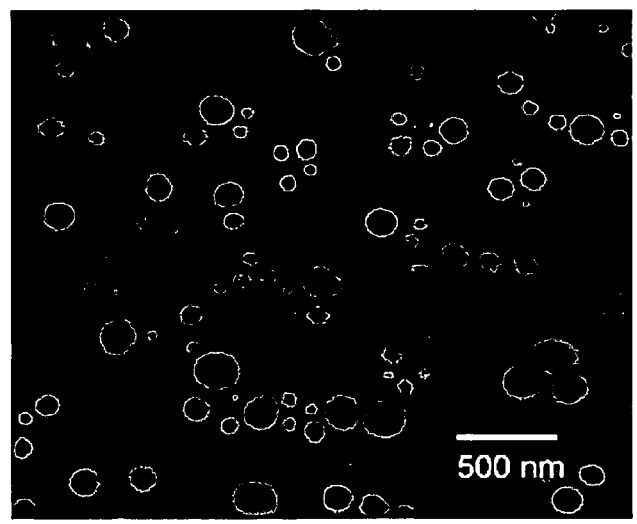
FIG. 22 is a ESEM micrograph of RM-synthesized nanoparticles.

FIG. 22 is an ESEM micrograph of nanoparticles obtained from a formulation comprising Dex-280 at 8 mg/ml and Con A at 50 mg/ml and $\phi_A$=0.10, $\phi_S$=0.25, and $\phi_O$=0.65. In this RM system, the particles obtained are much larger than the original aqueous domains, most probably due to the pH-dependent change in RM phase behavior. In addition, one would expect that the interaction between Con A and dextran increases droplet attraction, leading to particle growth. The entire population of particles is present in the submicron range, demonstrating our ability to restrict the reaction size domain and form physically crosslinked nanoparticles via RM-mediated synthesis.

Figure 23:
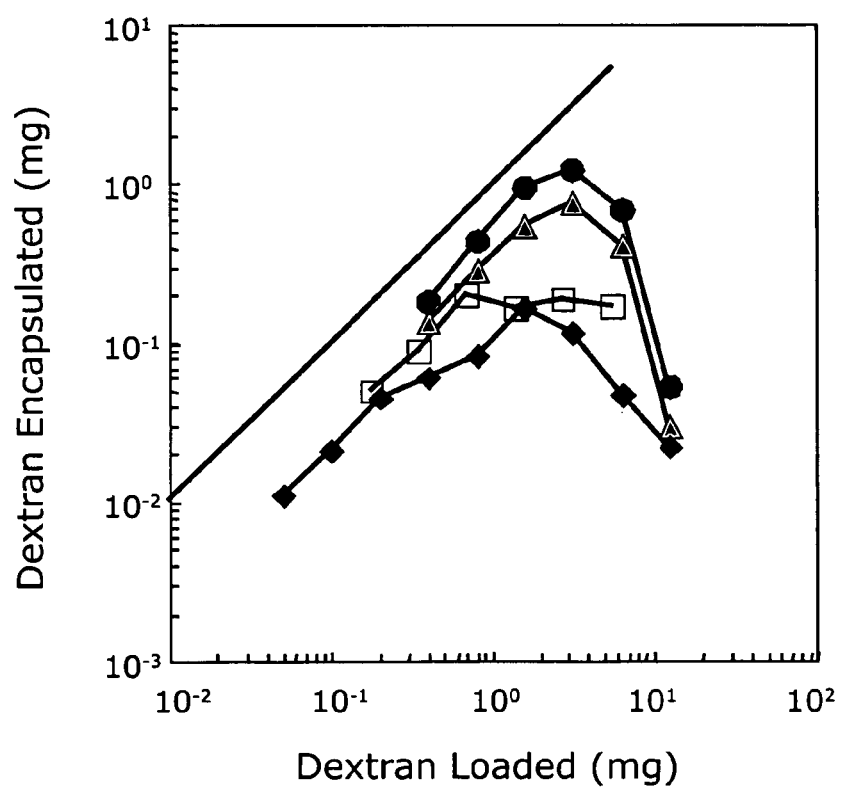
FIG. 23 is a graph illustrating nanoparticle crosslinking efficiency as the amount of dextran encapsulated vs. the amount loaded into the RM aqueous phase (square: Dex MW=40K, square: ManDex MW=40K, triangle: DexMW=280K, circle: ManDex MW=280K).
Figure 24:
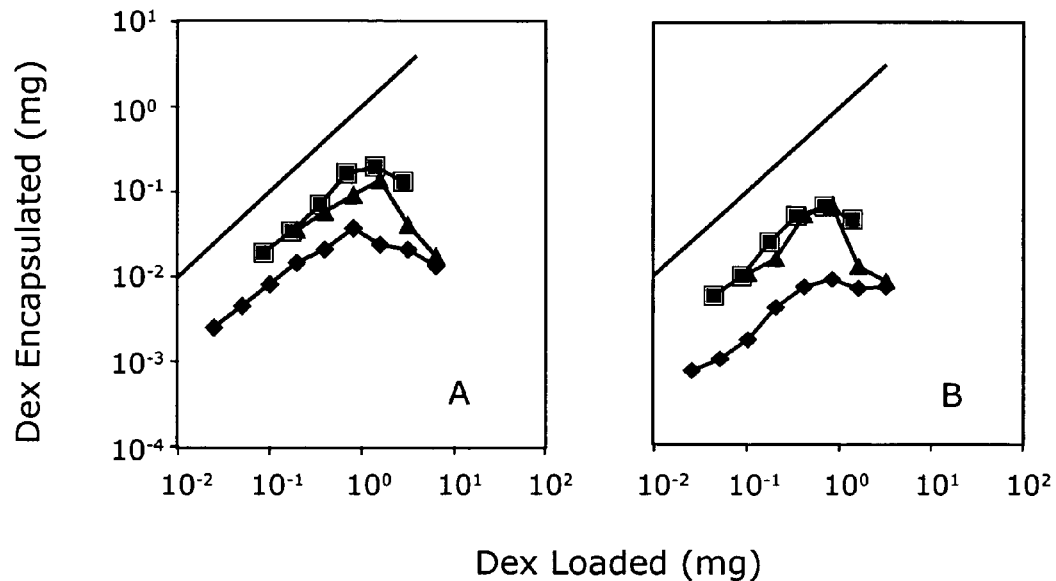
FIG. 24 is a graph illustrating nanoparticle crosslinking efficiency plotted as the amount of Dextran encapsulated vs. the amount loaded into the RM aqueous phase at a constant (A) [Con A]$_{aq}$=25 mg/ml and (B) 12.5 mg/ml (diamond: MW=40K, square: ManDex MW=40K, triangle: Dex MW=280K).

To evaluate the amount of dextran participating in the nanoparticle crosslinking reaction as a function of dextran molecular weight and Con A/dextran ratio, the dextrans were fluorescently labeled (FITC) as before to easily detect their concentration in solution. FIG. 23 illustrates the amount of crosslinked dextran versus the amount loaded into the RM for [Con A]$_{aq}$=50 mg/ml. As before, both Dex-40 and Dex-280 demonstrate a strong dependence of the amount of crosslinking on [Con A] (FIG. 24). The results show that as [dextran] decreases at a constant [Con A], the extent of crosslinking increases and reaches a maximum at [Con A]/[dextran] between 3 and 6. The amount of crosslinked polymer is improved by a factor of 5 by increasing the dextran MW to 280 K. Mannosylation of dextran of both MW's also results in a greater extent of crosslinking over a range of [Con A]/[dextran] ratios (FIGS. 23-24). The higher affinity of Con A for mannose ($K_{d,glucose}$=3.8$K_{d,mannose}$) ensures a higher proportion of bound polymer at a given concentration of Con A and dextran (J. N. Sanders, et al., *J. Inorg. Biochem.* 70, 71 (1998). In addition, mannosylation of the dextran backbone effectively increases the degree of branching, which is known to facilitate the precipitation reaction between Con A and α-1,6-linked polysaccharides (I. J. Goldstein, C. E. Hollerman, J. M. Merrick, *Biochim. Biophys. Acta* 97, 68 (1965)).

EXAMPLE 8

Glucose Sensitive Degradation of Nanoparticles

To obtain the IGS for nanoparticles of different composition, the isolated nanoparticles were redispersed in a known volume of pH 7.0 BES buffer containing 0.150 M NaCl and 1 mM $Mn^{2+}$ and $Ca^{2+}$ ions. The dispersion was mixed for 30 min at room temperature, followed by centrifugation for 30 min to separate the particles from the aqueous medium. Half the volume was collected for analysis and replaced with a higher concentration glucose buffer. The collected samples were analyzed using an fmax fluorescence spectrophotometer with $\lambda_{ex}$=485 nm and $\lambda_{em}$=538 nm to determine the amount of dextran dissolved from the nanoparticles after each step.

Figure 25:
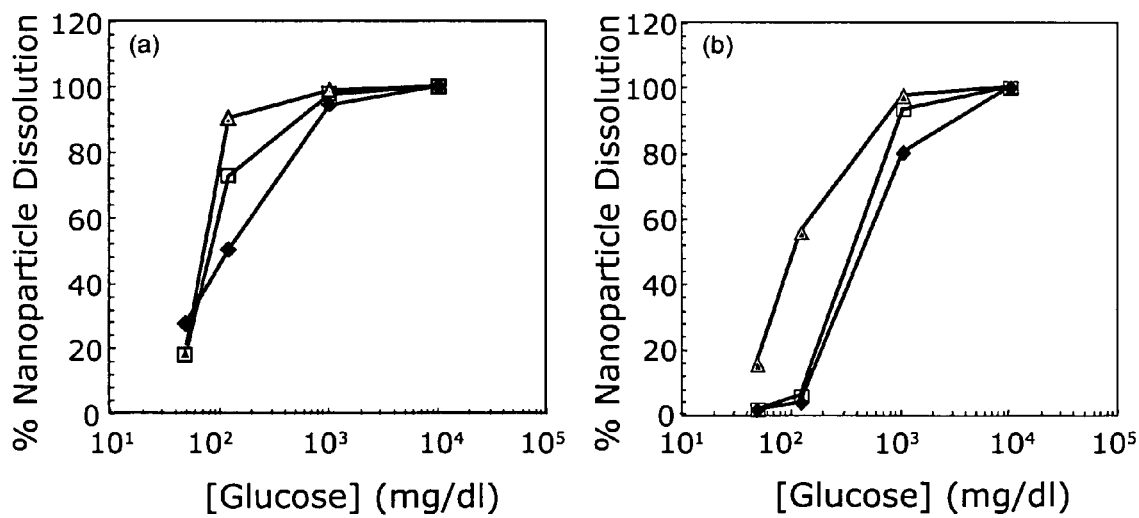
FIG. 25 is a series of graphs illustrating step-wise nanoparticle dissolution in pH 7.0 BES buffered saline solution to determine intrinsic glucose sensitivity for (A) dex MW=280K (B) ManDex MW=280K for Con A/dextran=1.6 (triangle), 3.1 (square), 6.2 (diamond) (w/w).

Plotting the percent of nanoparticle dissolution as a function of glucose concentration for the Dex-280 (FIG. 25) shows that glucose sensitivity may be controlled based on the relative ratio of Con A to polymer. Increasing the Con A/dextran from 1.6 to 6.3 (w/w) results in particles that are more sensitive to higher glucose concentrations. In addition, ManDex-280 nanoparticles have almost an order of magnitude higher IGS than unmodified nanoparticles. The combination of Con A/dextran ratio and degree of mannosylation provides a convenient means for fine tuning the nanoparticle glucose-sensitivity for any application. FIG. 26 shows that the degree of cross-linking strongly influences glucose sensitivity. Both insufficient and excess cross-link density greatly decrease the sensitivity of particle dissolution to glucose concentration. There is an optimal ratio of dextran 20 to Con A 22 where their interaction transitions from a dextran-limited regime to a Con A limited regime (FIG. 27). At this ratio, the dextran is cross-linked the most effectively, resulting in the highest dextran release upon increasing the glucose concentration.

Figure 28:
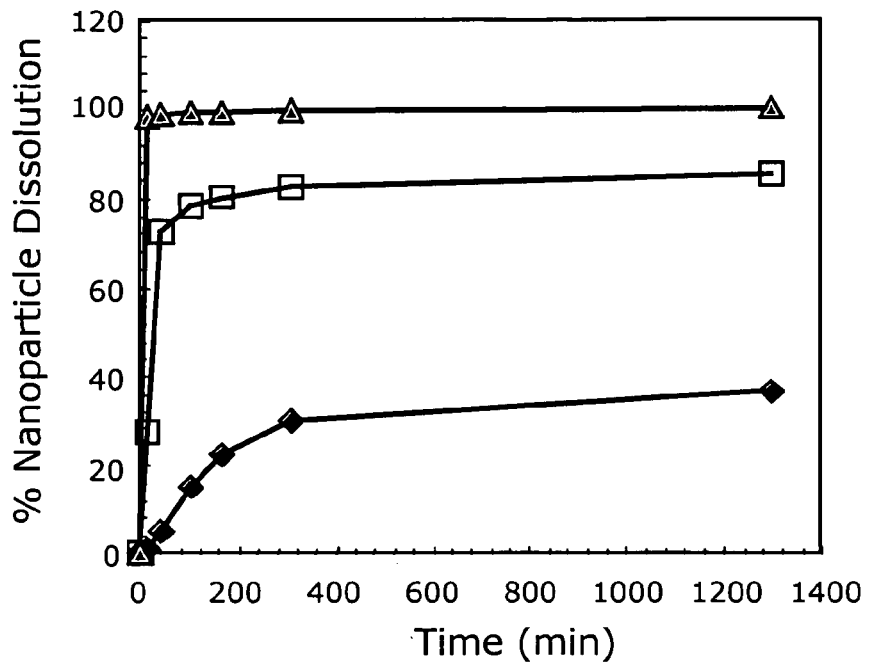
FIG. 28 is a graph illustrating room-temperature nanoparticle dissolution in pH 7.0 BES buffered saline solution at [glucose]=0 mg/dl (diamond), 100 mg/dl (square), and 1000 mg/dl (triangle).
Figure 29:
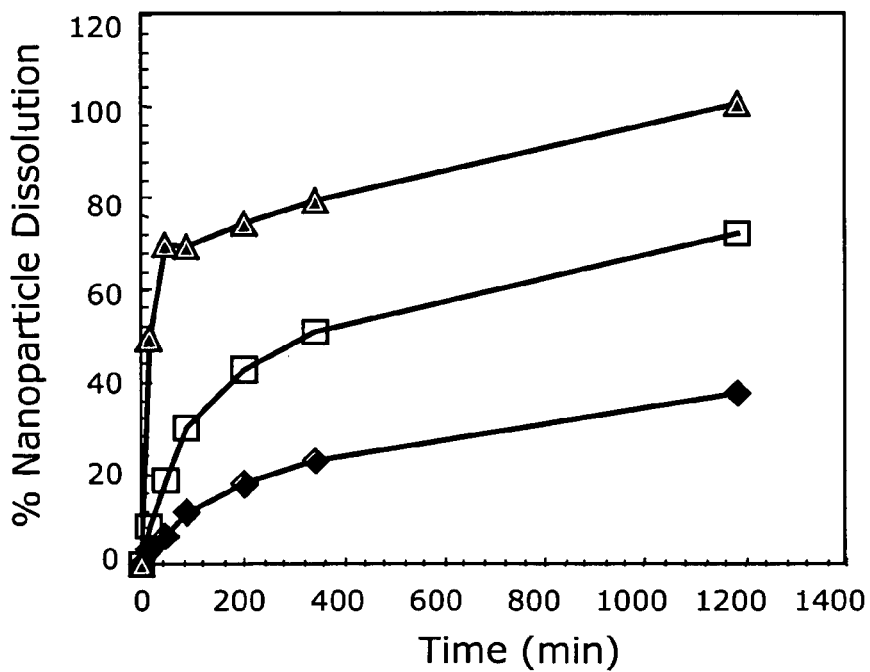
FIG. 29 is a graph illustrating room-temperature nanoparticle dissolution in pH 7.0 BES buffered saline solution at [glucose]=(diamond) 0 mg/dl, (square) 100 mg/dl, and (triangle) 1000 mg/dl.

Nanoparticles synthesized at a Con A/dextran ratio of 3.1 from Dex-280 (FIG. 28) and a Con A/dextran ratio of 6.1 from ManDex-280 (FIG. 29) were placed in 20 mM pH 7 buffered saline solutions containing 0, 100, and 1000 mg/dl glucose. Dissolution was measured by detecting dextran fluorescence in the supernatant and normalizing the calculated concentrations to those obtained after complete dissolution. As with the gels, the nanoparticles dissolve at markedly different rates depending on the glucose concentration in the release medium. Most importantly, the mannosylated nanoparticles demonstrate sustained dissolution over an entire day even at the extremely high glucose concentration of 1,000 mg/dl, while the unmodified nanoparticles completely dissolve in less than an hour at the same glucose concentration.

EXAMPLE 9

Figure 30:
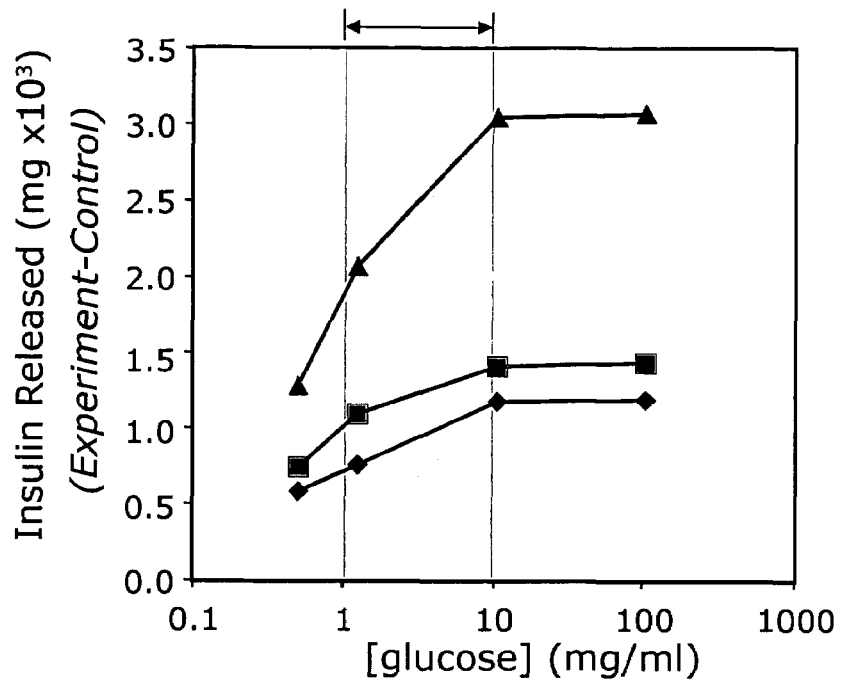
FIG. 30 is a graph illustrating glucose-responsive insulin release from particles prepared from FITC-Dex-42 with [Con A]$_{aq}$=50 mg/ml and [FITC-dex]aq=(triangle) 32 mg/ml, (square) 64 mg/ml, (diamond) 128 mg/ml.
Figure 31:
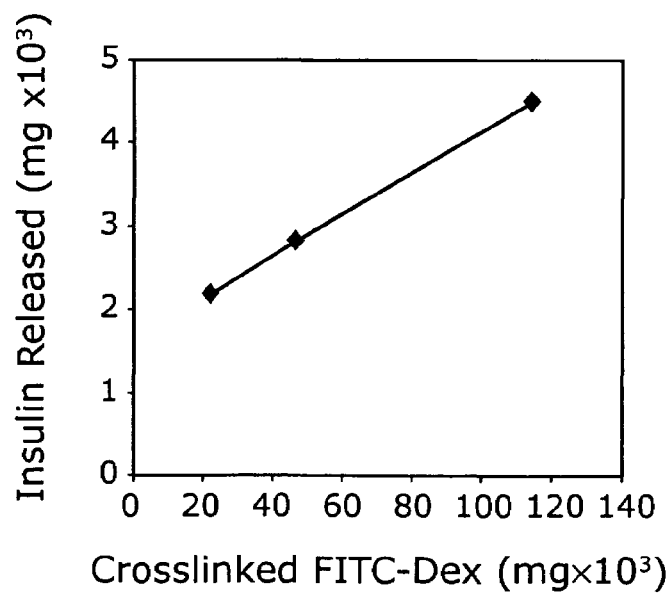
FIG. 31 is a graph illustrating the correlation between an amount of insulin released at the highest glucose concentration (e.g., insulin encapsulation) and the amount of FITC-Dex crosslinked for each specific formulation.

Release Profiles of Insulin-Containing Nanoparticles $Zn^{2+}$-free bovine insulin (Sigma-Aldrich) was dissolved in the aqueous phase of select compositions, and the amount released was determined by high-performance liquid chromatography (HPLC) using 37% $CH_3CN$ and 63% pH 2.4 $Na_2SO_4/H_3PO_4$ mobile phase. FIG. 30 shows that the particles are capable of encapsulating insulin and releasing it preferentially under hyperglycemic sugar concentrations. FIG. 31 further illustrates that more insulin is encapsulated and released as more polymer participates in crosslinking the particles.

EXAMPLE 10

Plant Lectins

*Pisum sativum agglutinin* (PSA), a lectin derived from the pea, was chosen as an alternative glucose-binding protein because of its reduced immunogenicity and mitogenicity. In one embodiment, 0.100 ml of PSA is dissolved at 50 mg/ml in 20 mM BES buffered saline containing 1 mM $Mn^{2+}$, 1 mM $Ca^{2+}$, and 1 M NaCl and added to 0.100 ml of a dextran solution that is dissolved at a known concentration in 20 mM BES buffered saline containing 150 mM NaCl. The solutions are allowed to react for one hour, after which the resulting gels are separated from the supernatant. The gels are washed twice with 1 ml of BES buffered saline solution and freeze-dried. To evaluate the amount of dextran participating in the gel reaction as a function of dextran molecular weight (MW) and Con A/dextran ratio, the dextrans are fluorescently labeled to easily detect their concentration in solution (MW 70 K and 170 K labeled with TRITC, MW 280 K and 500 K labeled with FITC. The fluorescence of each of the supernatants is measured using a Molecular Devices fmax fluorescence spectrophotometer (TRITC: $\lambda_{ex}$=544 nm, $\lambda_{em}$=590 nm; FITC: $\lambda_{ex}$=485 nm, $\lambda_{em}$=538 nm), and converted to concentrations using a set of standard curves. Crosslinking efficiency ($X_{CL}$) is calculated according to Equation 1.

EXAMPLE 11

Mammalian Lectins

MBP is dissolved in a pH 7 buffer at 1-100 mg/ml containing 10-100 mM calcium chloride ($CaCl_2$). The resulting solution is added to each of several dextran, mannosylated dextran, or yeast mannan solutions of varying concentrations. The crosslinking efficiency and glucose sensitivity of the resulting materials are determined as described above in Example 1. In select syntheses, insulin-dextran, insulin-mannose-dextran, or insulin-mannan conjugates bearing sufficient glucose or mannose residues may be combined with the concentrated MBP solutions to produce a gel capable of releasing insulin in a glucose-dependent manner. The insulin release may be monitored using the procedure described in Example 3.

EXAMPLE 12

Conjugation of a Sugar to a Carboxyl Bearing Polymer 12.5 mg of 100% carboxylated CBP is dissolved in 0.625 ml of 0.02 M sodium phosphate buffer, pH 4.5. To this solution, 0.625 ml of a 2% carbodiimide solution is added dropwise and mixed for 4 hours at room temperature. The resulting solution is dialyzed against 0.02 M sodium phosphate buffer, pH 4.5 to remove unreacted carbodiimide and then against a 0.2 M borate buffer, pH 8.5. To the resulting solution, 0.5-2.5 mg of mannosamine (MA) or glucosamine (GA) is added and mixed gently overnight at room temperature. 0.050 ml of a 0.25 M ethanolamine solution is then added to block unreacted sites. The resulting solution is dialyzed against deionized water and freeze dried to obtain glycosylated-CBP.

EXAMPLE 13

Conjugation of a Sugar to a Carboxyl Bearing Polymer

Sufficient CBP (COOH form) to provide 300 micromoles of carboxylate groups is dried under high vacuum over $P_2O_5$ and then dissolved in 2 ml of dry dimethylsulfoxide (DMSO). 50 micromoles of tributylamine (TBA) and 50 micromoles of isobutylchloroformate are added at room temperature, and mixed under argon atmosphere for 15 minutes. 10-100 micromoles of GA or MA are added separately to 3 ml of dry DMSO, then mixed with the CBP solution, and stirred overnight. The mixtures are then diluted in three volumes of ice cold water, dialyzed against 0.02% ammonium bicarbonate to remove uncoupled GA or MA, and freeze-dried to obtain dry CBP-GA or CBP-MA conjugates (modified from Baudys, et al., *Bioconjugate Chem.*, 9, 176-183 (1998), the contents of which are incorporated herein by reference). In select syntheses, the remaining COOH groups are capped with OH groups by employing the above procedure with an excess of ethanolamine (EA).

EXAMPLE 14

Covalent Attachment of Insulin to A Biodegradable Polymer

Insulin may be conjugated to CBP as described by Baudys, 1998. Sufficient CBP (COOH form) to provide 300 micromoles of carboxylate groups is dried under high vacuum over $P_2O_5$ and then dissolved in 2 ml of dry dimethylsulfoxide (DMSO). 50 micromoles of tributylamine (TBA) and 50 micromoles of isobutylchloroformate are added at room temperature, and mixed under argon atmosphere for 15 minutes. 25 micromoles of insulin are added separately to 3 ml of dry DMSO, then mixed with the CBP solution, and stirred overnight. The mixtures are then diluted in three volumes of ice cold water, dialyzed against 0.02% ammonium bicarbonate, and freeze-dried to obtain dry CBP-insulin conjugates. Conjugated insulin is then separated from unconjugated insulin using a high-load preparative HPLC size exclusion column (e.g. Superdex 75) and freeze-dried to obtain pure insulin-CBP conjugates.

EXAMPLE 15

Conjugation of a Sugar to an Aminated Scaffold

A method for conjugating sugars to —$NH_2$ groups is described in Thoma, et al., *J. Am. Chem. Soc.*, 121, 5919-5929 (1999). Briefly, NBP (1 mmol based on —$NH_2$ groups) is suspended in a mixture of dimethylformamide (DMF) and 1 ml of 2,6-lutidine under a dry argon atmosphere. At 0° C., a solution of acid anhydride (3.0 mmol) in 1 ml of DMF is added within 15 minutes, and the resulting clear solution stirred for 16 hr at 0° C. The product is precipitated by dropwise addition to 40 ml of a stirred 1:1 mixture of ethanol and ether. The solid is filtered, washed, and dried under vacuum. 10.0 mg (0.050 mmol) of dried solid is dissolved in 2 ml of DMF containing 2 equivalents of thioglucose (varying alpha/beta anomer ratio), obtained from Sigma Aldrich. Triethylamine is then added at 2 equivalents and stirred at room temperature for 16 h. The mixture is then added dropwise to 30 ml of a 1:1 mixture of ethanol and ether. The precipitate is washed with ethanol and dried under vacuum. The crude product may then be dissolved in deionized water and ultrafiltered exhaustively against fresh deionized water, followed by lyophilization to produce dry NBP-glucose polymer. The degree of glycosylation is easily adjusted by varying the equivalents of thioglucose used in the reaction mixture. In this case, the unreacted —$NH_2$ groups are capped with glycerol by adding an excess (3.0 to 5.0 equivalents) of thioglycerol, obtained from Sigma Aldrich.

EXAMPLE 16

Conjugation of a Sugar to a Hydroxylated Scaffold

OBP may be modified with sugars such as glucose or mannose using the same DVS procedure used to synthesize mannosylated-dextran. Briefly, OBP is added to a pH 11.4 bicarbonate buffer and activated with DVS. D-mannose or D-glucose is then added and allowed to react for ~1 hour at room temperature, after which glycine is added to neutralize and quench the reaction. The resulting polymer is dialyzed exhaustively against deionized water and finally lyophilized to obtain glycosylated-OBP.

EXAMPLE 17

Conjugation of a Sugar to a Hydroxylated Scaffold

OBP may also be modified with sugars using periodate coupling as described in Mislovicová, et al., *Bioconjugate Chem.*, 13, 136-142 (2002), the contents of which are incorporated herein by reference. 100 mg of OBP is dissolved in 1-3.5 ml of a 0.05 M aqueous solution of sodium periodate ($NaIO_4$) and stirred in the dark at 4° C. for one hour. The volume of periodate solution is varied depending on the degree of hydroxylation of the OBP and the desired extent of reaction. The reaction is stopped by adding 1 ml of ethylene glycol and stirring for one hour. The resulting mixture is dialyzed against water and lyophilized. The resulting dry dialdehyde form of OBP is dissolved in 4 ml of a 0.05 M phosphate buffer, pH 7 at 10 mg/ml. To this solution, 4 ml of a solution of GA or MA in 0.05 M phosphate buffer, pH 7 at 10-50 mg/ml is added along with 2.5 ml of a 10 mg/ml sodium cyanoborohydride ($NaCNBH_3$) solution and the resulting mixture stirred at room temperature for 24 hours. The reaction is then stopped by adding a sodium borohydride ($NaBH_4$) solution in 0.05 M pH 9.5 borate buffer at a concentration of 5 mg/ml to reduce the remaining aldehyde groups. The resulting mixture is stirred for 6 hours at room temperature, after which the pH is adjusted to 7 using 4 M hydrochloric acid (HCl). The resulting solution is ultrafiltered exhaustively against deionized water and lyophilized to obtain pure glycosylated-OBP. In this embodiment, equal volumes of the two reactant (polymer and sugar) solutions are employed to prevent the components from reacting too quickly. The degree of conjugation is controlled by adjusting the concentrations of the solutions.

EXAMPLE 18

Conjugation of Insulin to a Hydroxylated Polymer

Insulin may be conjugated to OBP using the same CNBr method that was used to conjugate insulin to dextran. This conjugation involves activating dextran with cyanogen bromide (CNBr) at pH 10 in water, followed by reaction with insulin (L. Kagedal, S. Akerstrom, *Acta. Chem. Scand.* 25, 1855 (1971)).

EXAMPLE 19

Conjugation of Insulin Secretogues to a Polysaccharide

Kagedal and Akerstrom describe that proteins and peptides containing free amino groups and also other amino compounds may be coupled to dextran by the CNBr method used to conjugate insulin (Kagedal and Akerstrom, 1971). In such a way, the peptides GLP-1 or exanitide may be coupled to dextran or mannosylated dextran, condensed with the appropriate multivalent glucose binding protein such as Con A or MBL, and released from the structure in a glucose-dependent manner to prevent adverse hypoglycemia caused by administration of these compounds in a non-glucose-dependent manner.

Sulfonylureas (SU), such as glibenclamide, are conjugated to OBP's according to the procedure outlined in S. Kim, et al.

*Biomaterials.* 24, 4843 (2003). Briefly, the OBP is dissolved in dimethylsulfoxide (DMSO) with SU and reacted by means of N',N'-dicyclohexylcarbodiimide (DCC) and 4-dimethylaminopyridine (DMAP) as catalysts. The reaction is carried out for 48 hours under argon and the dicyclohexylurea removed by filtration. The product is precipitated in ethanol, then dissolved in water, and filtered to remove insoluble particles. Following lyophilization, the product is further purified by dialysis, and lyophilized to obtain a pure OBP-SU product. In fact, an SU-conjugated pullulan obtained by this procedure was shown to possess dose-dependent insulinotropic action (Kim et al., 2003).

EXAMPLE 20

Conjugation of an Antibiotic to a Polysaccharide

Using the Kagedal and Akerstrom CNBr conjugation procedure, antibiotic-dextran conjugates, such as ampicillin-dextran, containing approximately 300 micromol/g were prepared and found to have significant bacteriostatic capability. Antibiotic-dextran conjugates are then crosslinked with Con A or any of the other multivalent glucose-binding proteins described above. The antibiotic-dextran is then released in a glucose-dependent manner to provide long-term, mealtime dosing of antibiotics with a single administration.

EXAMPLE 21

Conjugation of an Anticancer Drug to a Polysaccharide

A method for conjugating the chemotherapy agent, doxorubicin (DOX) to dextran is described in Dillman, et al., *Cancer Research*, 46, 4886-4891 (1986). Briefly, dextran is oxidized with periodate to form a polyaldehyde. The primary amine groups of DOX are reacted with the aldehyde groups on the dextran to form Schiff's bases. This preparation is then reduced with sodium borohydride. The conjugate may be purified using Sephadex G100 gel filtration followed by lyophilization to obtain purified Dextran-DOX conjugate. Ohya, et al., *Biomacromolecules*, 2, 927-933 (2001) describes a method for conjugating the chemotherapy agent, cisplatin, to dextran. Briefly, a dicarboxymethyl-dextran (DCM-Dex) intermediate is synthesized using diethyl bromomalonate in tetrahydrofuran (THF). Cisplatin (CDDP) is precipitated in silver nitrate solution to obtain CDDP (nitrato) and passed through an anion-exchange resin to convert to CDDP (hydroxo). This solution is then reacted with DCM-Dex solution in water and purified by gel-filtration over Sephadex G-25 and freeze-dried to obtain purified DCM-Dex/CDDP conjugate. In one embodiment, the anticancer drug-dextran conjugate may be crosslinked with Con A or any of the other multivalent glucose-binding proteins described above. The anticancer drug-dextran is then released in a glucose-dependent manner to provide long-term, mealtime dosing of chemotherapy with a single administration.

EXAMPLE 22

Cleavable Therapeutic Agent Conjugates with Polysaccharides

To increase biological activity or decrease plasma residence time, it may be preferred to release the therapeutic agent from a polymer-agent conjugate. Cleavable polymer-agent conjugates may be synthesized by linking the therapeutic agent to the polymer backbone through a peptide spacer that can be cleaved rapidly once present in the systemic circulation. For example, dipeptidyl peptidase IV (DP-IV), a transmembrane glycoprotein, is broadly distributed throughout the body and cleaves preferentially Xaa-Pro dipeptides from oligopeptides with lengths <30 amino acids (Engel, et al., PNAS, 100, 5063-5068 (2003)).

Carboxymethyldextran (CMDex) is synthesized according to the procedure of Huynh (Huynh, et al., Die Angewandte Makromolekulare Chemie, 254, 61-65 (1998)). Briefly, 2.0 g of dextran are slurried in 42.5 ml of tert-butanol. 7.5 ml of a 3.8 M sodium hydroxide solution is then added slowly followed by continuous stirring for one hour at room temperature. Then monochloroacetic acid (MCA) is added up to a [MCA]/[Dextran] ratio of 2.5 while stirring to complete homogeneity. After a 90 minute reaction at 60° C., the mixture is cooled, neutralized with acetic acid, precipitated in methanol, filtered, and dried under vacuum.

A Boc-glycyl-glycyl-pro-glycyl (Boc-Gly-Gly-Pro-Gly) may be obtained commercially or chemically synthesized using the Merrifield resin procedure (R. B. Merrifield Science 150, 178 (1965)). In one procedure (M. Harada, et al. J Control Release. 69, 399 (2000)), Boc-Gly-Gly-Pro-Gly is condensed with an amine-containing therapeutic agent (e.g. insulin-$NH_2$, GLP-1-$NH_2$, campotothecin-$NH_2$, doxorubicin-$NH_2$) in DMF at room temperature in the presence of 1-(3-dimethylaminopropyl)-3-ethyl-carbodiimide hydrochloride and triethylamine. The tert-butoxycarbonyl amide (N-Boc) protecting group is removed with hydrochloric acid in dioxane in an ice-bath. The resulting drug-linker is added to CMDex in water in the presence of 1-(3-dimethylaminopropyl)-3-ethyl-carbodiimide hydrochloride and reacted below 10° C. for two hours at pH 5.5. The resulting Drug-NH-Gly-Pro-Gly-Gly-CMDex conjugate is precipitated in ethanol, filtered, washed, and dried.

In one embodiment, an insulin-NH-Gly-Pro-Gly-Gly-CMDex (Ins-Link-Dex) conjugate is combined with a multivalent glucose-binding proteins to form a gel that degrades to release Ins-Link-Dex in a glucose-dependent manner. The Ins-Link-Dex is absorbed into systemic circulation where it is rapidly cleaved by DP-IV into free insulin and free CMDex. The free insulin then acts on hepatic and adipose tissue with full biological activity and circulation time.

EXAMPLE 23

Scaffold-Engineered Ligand-Binding Proteins—Lactate-Responsive Delivery

Other ligand-binding proteins may be synthesized by rational computational design followed by site directed mutagenesis of ligand-binding proteins as described in Looger et al., 2003, the contents of which are incorporated herein by reference. In one example, a soluble L-Lactate binding protein was synthesized with high affinity and specificity. Modifications to wild-type glucose binding protein (GBP), ribose binding protein (RBP), arabinose-binding protein (ABP), glutamine binding protein (QBP), and histidine binding protein (HBP) produce a binding site that selectively binds L-lactate (FIG. 36). The L-lactate binding protein is made multivalent by attaching several protein molecules to a polymer using the procedures of Example 14 or 18.

Dextran containing lactate oligomers is synthesized according to the procedure of de Jong (de Jong, et al., Journal of Controlled Release, 71, 261-275 (2001)). Briefly, a lactic acid oligomer is synthesized via ring-opening polymerization of lactide with 2-(2-methoxyethoxy)ethanol (MEE) and stannous octoate as initiator and catalyst, respectively. After activation of the hydroxyl end group of the oligomer with N,N'-carbonyldiimidazole (CDI) in tetrahydrofuran (THF) at room temperature for four hours, the resulting lactate-Cl is coupled to dextran. The coupling is performed at ambient temperature for four days in dimethylsulfoxide (DMSO) using 4-(N,N-dimethylamino)pyridine (DMAP) as a catalyst.

Dextran-lactate may be condensed with multivalent lactate-binding protein to produce a lactate-responsive delivery system. Elevated L-lactate concentrations are indicative of several medical conditions including extreme muscle fatigue. In one example, a molecule capable of stimulating expression and/or increasing activity of the monocarboxylate lactate transporter (Halestrap, et al., Biochem. J, 343, 281-299 (1999)) is encapsulated in dextran-lactate cross-linked with multivalent lactate-binding protein. The molecule is then released in a L-lactate dependent fashion to remove rapidly remove the metabolite from circulation.

EXAMPLE 24

Production of N-desulfated N-acetylated Heparin

One gram of heparin is dissolved in 30 ml water and applied to a column of [BIO-RAD AG50 W=X8 ($H^+$)] resin. The pass-through fraction eluted with water is neutralized immediately with pyridine and dialyzed overnight with distilled water at 4° C. This is lyophilized to obtain 1.0 g of heparin pyridinium salt. Complete N-desulfation of 500 mg of the salt is achieved through solvolysis as described by Danishefsky, "Methods in Carbohydrate Chemistry", Vol V, 1980, pp407-409, the contents of which are incorporated herein by reference, and Nagasawa, "Methods in Carbohydrate Chemistry,", Vol. VIII, 1980, pp291-294, the contents of which are incorporated herein by reference. N-acetylation of the de-N-sulfated heparin is performed according to Danishefsky (1980) (Sugahara, 2001).

EXAMPLE 25

Production of Carboxymethylated Dextran

Two grams of DexT10 (Extrasynthese Co.) is dissolved in 40 ml of water. 6.8 g of NaOH is added and the mixture chilled on ice. After adding 9.4 g of chloracetic acid, the mixture is stirred at room temperature for 20 h to obtain the sodium salt of CMDex (Sugahara, 2001).

EXAMPLE 26

Production of Carboxymethylated Dextran

Dextran having a molecular weight between 10,000 and 40,000 is dissolved in tert-butanol, isopropanol, 1,1,3,3 tetramethylurea, or a mixture of DMSO and tetramethylurea. Sodium hydroxide solution of a concentration in the 2M-8M range is added slowly and stirred for 1 hour at room temperature. Where a solvent other than tert-butanol is used, the solvent/water ratio is about 85:15. Monochloroacetic acid is added until [MCA]/[dextran] is in the range of 1-3.5 while stirring to maintain homogeneity. The mixture is maintained at 60° C. for up to 240 mins. The mixture is then cooled to room temperature and neutralized with glacial acetic acid. The chloromethylated product is then precipitated with methanol (Huynh, 1998).

EXAMPLE 27

Production of a Galactose Responsive Drug Delivery System

Galactosamine is linked to a CBP using the techniques of Examples 12 or 13, or galactose is linked to an OBP using the techniques of Example 18. The recombinant galactose-binding lectin subunit developed by Medina-Bolivar et al., *Vaccine* 21, 997 (2003), the contents of which are incorporated by reference, is attached to a biodegradable polymer to form a polyfunctional lectin. The polyfunctional lectin and the galactosylated polymer are mixed in the presence of galactose transferase to form a gel. The gel may be used to treat galactosemia. An increase in the galactose concentration in serum will cause the gel to degrade and release the enzyme. Other galactose-specific lectins include ricin, mistletoe galactose-binding lectin ML-1, and abrin. The galactose-binding subunit should be purified from the toxic subunits before incorporation into a gel for use with the invention.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A material for delivery of a therapeutic agent in response to an indicator, comprising:
   conjugates that include a therapeutic agent covalently linked to a polymer, wherein the polymer includes two or more indicator analogs; and
   polyfunctional cross-linking agents that cross-link conjugates by non-covalently interacting with indicator analogs on different conjugates, wherein:
   the material is insoluble in the absence of an indicator that competes with the indicator analogs for non-covalent interactions with the cross-linking agents;
   conjugates are released from the material in the presence of the indicator at a rate that varies within physiological concentrations of the indicator;
   the indicator is glucose;
   the indicator analogs comprise glucose and/or mannose residues; and
   the therapeutic agent is insulin or an insulin secretogue.

2. The material of claim 1 wherein the polyfunctional cross-linking agents are covalently linked to the polymer.

3. The material of claim 1 wherein the material is comprised of a plurality of particles.

4. The material of claim 3 wherein the particles have a size from about 100 nm to about 300 nm.

5. The material of claim 3 wherein the particles have a size from about 300 nm to about 500 nm.

6. The material of claim 3 wherein the particles have a size from about 500 nm to about 5 µm.

7. The material of claim 3 wherein the particles have a size from about 5 µm to about 50 µm.

8. The material of claim 3 wherein the particles have a size from about 50 µm to about 100 µm.

9. The material of claim 1 wherein the therapeutic agent is covalently linked to the polymer by a bond that is susceptible to enzymatic cleavage.

10. The material of claim 1 wherein the indicator analog is a portion of a side group of the polymer.

11. The material of claim 1 wherein the polymer is derivatized with the indicator or the indicator analog.

12. The material of claim 1 wherein the indicator analog is incorporated into the backbone of the polymer chain.

13. The material of claim 1 wherein the polymer is selected from poly(lactic acid) (PLA), poly(glycolic acid) (PGA), PLA-PGA co-polymers (PLGA), poly(anhydrides), poly(hydroxy acids), poly(ortho esters), poly(propylfumerates), poly (caprolactones), polyamides, polyamino acids, polyacetals, biodegradable polycyanoacrylates, biodegradable polyurethanes, polysaccharides, co-polymers of the above, adducts of the above, and mixtures of the above.

14. The material of claim 1 wherein the polymer is selected from carboxylated polysaccharides, —NH2 pendant polysaccharides, hydroxylated polysaccharides, alginate, collagen-glycosaminoglycan, collagen, dextran, pullulan, mannan, amylose, amylopectin, glycogen, cellulose, hyaluronate, chondroitin, dextrin, chitosan, co-polymers of aminated and non-aminated amino acids, co-polymers of hydroxylated and non-hydroxylated amino acids, co-polymers of carboxylated and non-carboxylated amino acids, co-polymers of the above, adducts of the above, and mixtures of the above.

15. The material of claim 1 wherein the polyfunctional cross-linking agents include a protein selected from phytohemoagglutinins, human mannan binding protein (MBP), human pulmonary surfactant protein A (SP-A), human pulmonary surfactant protein D, CL-43 and conglutinin.

16. The material of claim 15 wherein the phytohemoagglutinin is selected from concanavalin A (Con A) and phytohemoagglutinins derived from pisum sativum (pea), lathyrus odoratus (sweet pea), lens culinaris (lentil), narcissus pseudonarcissus (daffodil), vicia faba (fava bean), and vicia sativa (garden vetch).

17. The material of claim 1 wherein the polyfunctional cross-linking agents include a polyfunctional binding protein.

18. The material of claim 1 wherein the polyfunctional cross-linking agents include a plurality of monofunctional binding proteins or binding fragments of proteins linked to one another.

19. The material of claim 18 wherein the polyfunctional cross-linking agents include a plurality of monofunctional binding proteins or binding fragments of proteins covalently attached to a polymer.

20. The material of claim 1 further comprising a fluorophore.

21. The material of claim 20 wherein the fluorophore is covalently or non-covalently linked to the polymer, the therapeutic agent, or a polyfunctional cross-linking agent.

22. The material of claim 1 wherein the polymer is a polysaccharide and the polyfunctional cross-linking agents include a plant lectin or a mammalian analog to a plant lectin.

23. The material of claim 1 wherein the polymer is dextran or mannose-derivatized dextran, the polyfunctional cross-linking agents include concanavalin A, and the therapeutic agent is insulin.

24. The material of claim 1 wherein the polyfunctional cross-linking agents are not covalently linked to the polymer.

25. The material of claim 24 wherein the polymer is a polysaccharide, the polyfunctional cross-linking agents include a lectin, and the therapeutic agent is insulin.

26. The material of claim 1 wherein the polyfunctional cross-linking agents include concanavalin A.

27. The material of claim 1 wherein the polyfunctional cross-linking agents include a chemically modified concanavalin A.

28. The material of claim 1 wherein the polyfunctional cross-linking agents include a pegylated concanavalin A.

29. The material of claim 1 wherein the therapeutic agent is insulin

30. The material of claim 1 wherein the therapeutic agent is an insulin secretogue.

31. The material of claim 30 wherein the insulin secretogue is a sulfonylurea.

32. The material of claim 31 wherein the sulfonylurea is glibenclamide.

33. The material of claim 30 wherein the insulin secretogue is GLP-1 or a GLP-1 analogue.

34. The material of claim 33 wherein the GLP-1 analogue is exanitide.

35. The material of claim 1 wherein the indicator analog includes glucosamine or mannosamine.

36. The material of claim 1 wherein the polyfunctional cross-linking agents bind glucose and mannose.

37. A method comprising administering a material of claim 1 to a patient.

38. The method of claim 37 wherein the material is administered by subcutaneous injection.

39. The method of claim 37 wherein the polyfunctional cross-linking agents include concanavalin A.

40. The method of claim 37 wherein the polyfunctional cross-linking agents include a chemically modified concanavalin A.

41. The method of claim 37 wherein the polyfunctional cross-linking agents include a pegylated concanavalin A.

42. The method of claim 37 wherein the therapeutic agent is insulin

43. The method of claim 37 wherein the therapeutic agent is an insulin secretogue.

44. The method of claim 43 wherein the insulin secretogue is a sulfonylurea.

45. The method of claim 44 wherein the sulfonylurea is glibenclamide.

46. The method of claim 37 wherein the insulin secretogue is GLP-1 or a GLP-1 analogue.

47. The method of claim 46 wherein the GLP-1 analogue is exanitide.

48. The method of claim 37 wherein the indicator analog includes glucosamine or mannosamine.

49. The method of claim 37 wherein the polyfunctional cross-linking agents bind glucose and mannose.

* * * * *